(12) United States Patent
Tanaka et al.

(10) Patent No.: US 8,979,759 B2
(45) Date of Patent: Mar. 17, 2015

(54) ULTRASONIC IMAGING DEVICE AND INFORMATION PROCESSING DEVICE

(75) Inventors: Tomohiko Tanaka, Hachioji (JP); Takashi Azuma, Fuchu (JP); Marie Tabaru, Hino (JP); Kunio Hashiba, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 26 days.

(21) Appl. No.: 13/521,776

(22) PCT Filed: Feb. 2, 2011

(86) PCT No.: PCT/JP2011/052116
§ 371 (c)(1),
(2), (4) Date: Jul. 12, 2012

(87) PCT Pub. No.: WO2011/102221
PCT Pub. Date: Aug. 25, 2011

(65) Prior Publication Data
US 2012/0296209 A1    Nov. 22, 2012

(30) Foreign Application Priority Data

Feb. 17, 2010  (JP) ................................. 2010-032429

(51) Int. Cl.
*A61B 8/04* (2006.01)
*A61B 8/08* (2006.01)
*A61B 8/14* (2006.01)

(52) U.S. Cl.
CPC .................. *A61B 8/0883* (2013.01); *A61B 8/04* (2013.01); *A61B 8/485* (2013.01)
USPC .......................................... 600/438; 600/443

(58) Field of Classification Search
USPC .................................. 600/437, 438, 443, 450
See application file for complete search history.

(56) References Cited

U.S. PATENT DOCUMENTS 5,840,028 A    11/1998    Chubachi et al.

FOREIGN PATENT DOCUMENTS

JP    10-5226    1/1998

OTHER PUBLICATIONS

S. H. Advani et al. Free vibrations of fluid-filled spherical shells, J. Sound Vib. (1970) 12(4), 453-462.

(Continued)

*Primary Examiner* — Michael Rozanski
(74) *Attorney, Agent, or Firm* — Baker Botts LLP

(57) ABSTRACT

Ultrasonic imaging device noninvasively measures cardiac muscle stiffness or intracardiac pressure. The device includes: an ultrasonic probe (2) transmitting and receiving ultrasonic waves to and from the heart; a signal-processing section (15) processing reflected echo signals; a display section (14) displaying results of signal processing as an image; and an input section (10) setting a predetermined point on the image. The signal-processing section (15) includes: a shape-extracting section (152) perceiving information on the shape of the heart from the reflected echo signals; a natural-frequency detecting section (153) detecting natural frequency of the heart from the reflected echo signals; and a calculating section (154) calculating stiffness of the cardiac muscle or the intracardiac pressure, wherein the calculating section (154) accurately calculates the stiffness of the cardiac muscle from the natural frequency of the heart and calculates the intracardiac pressure from the stiffness of the cardiac muscle that has been calculated.

13 Claims, 16 Drawing Sheets

(56) References Cited

OTHER PUBLICATIONS

Hideyuki Honda et al., Noninvasive measurement of left ventricular myocardial elasticity, The American Physiological Society, 1994, pp. H881-H890.

M. Sato et al., Method for noninvasive estimation of left ventricular end diastolic pressure based on analysis of heart wall vibration, Electronics Letters, May 23, 1996, pp. 949-950, vol. 32, No. 11.

Israel Mirsky et al. Evaluation of Passive elastic Stiffness for the Left Ventricle and Isolated heart Muscle, Chapter eleven (1974), pp. 331-359.

JP Office Action for Japanese Application No. 2012-500547, issued on Jan. 8, 2013.

Hiroshi Kanai, "Noninvasive Measurement of Spatial Distribution of Small Vibrations in Heart Wall", Journal of Medical Ultrasonics, Apr. 1999, vol. 26, No. 4, p. 670.

Hiroshi Kanai, "Imaging Spatial Distribution of High-Frequency Small Vibrations on the Heart Wall", Proc. IEEE Ultrason. Symp., 1998, vol. 2, pp. 1689-1692.

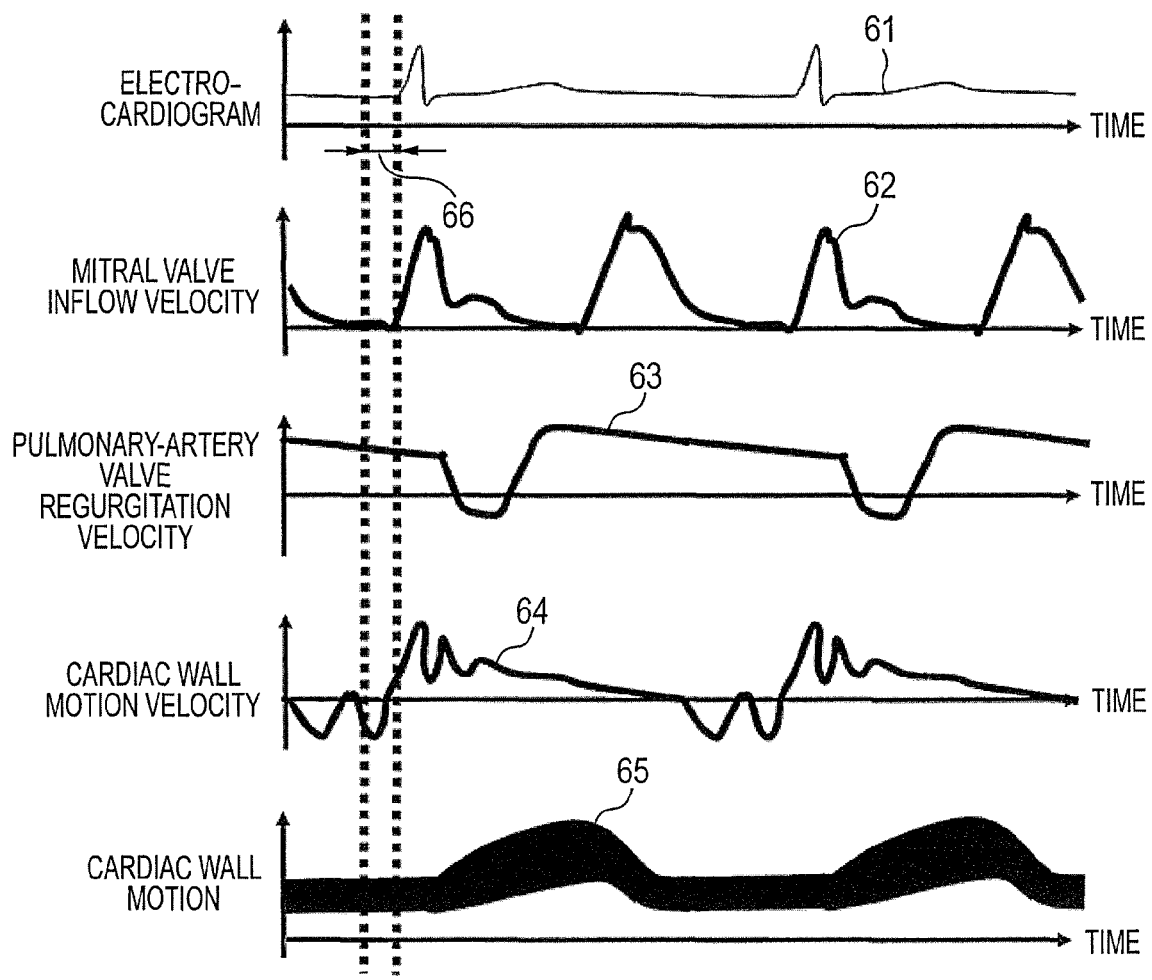
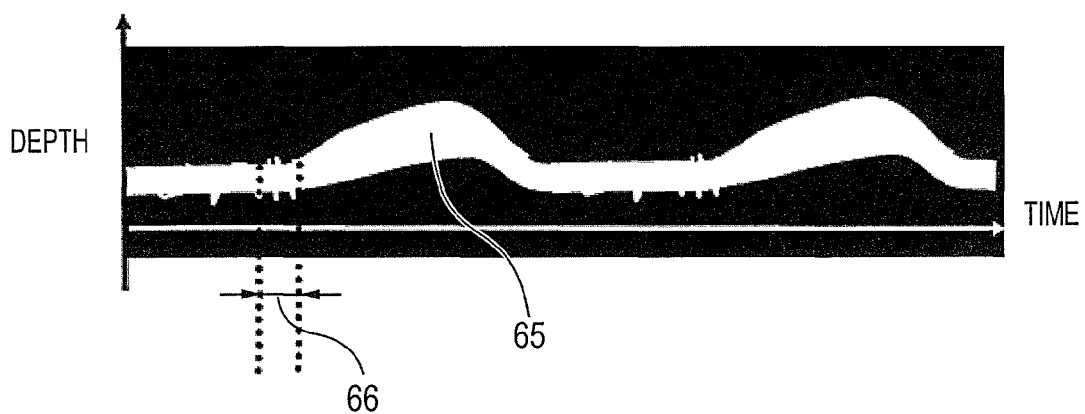

FIG. 6
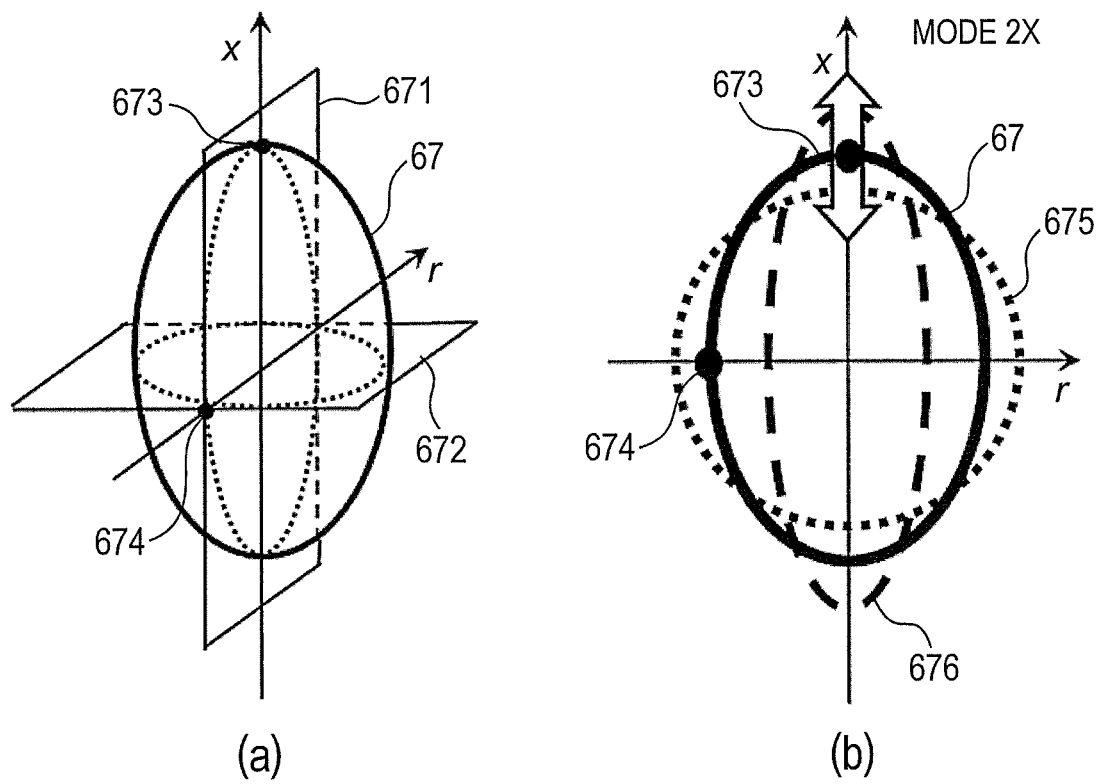
(a)
(b)
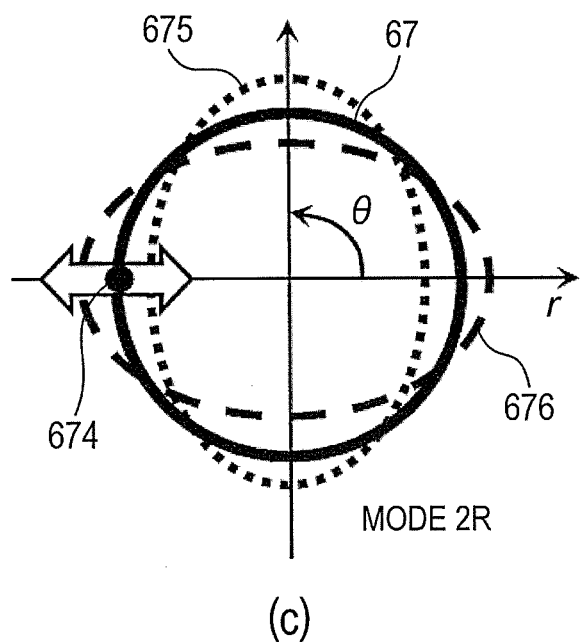
(c)

FIG. 7
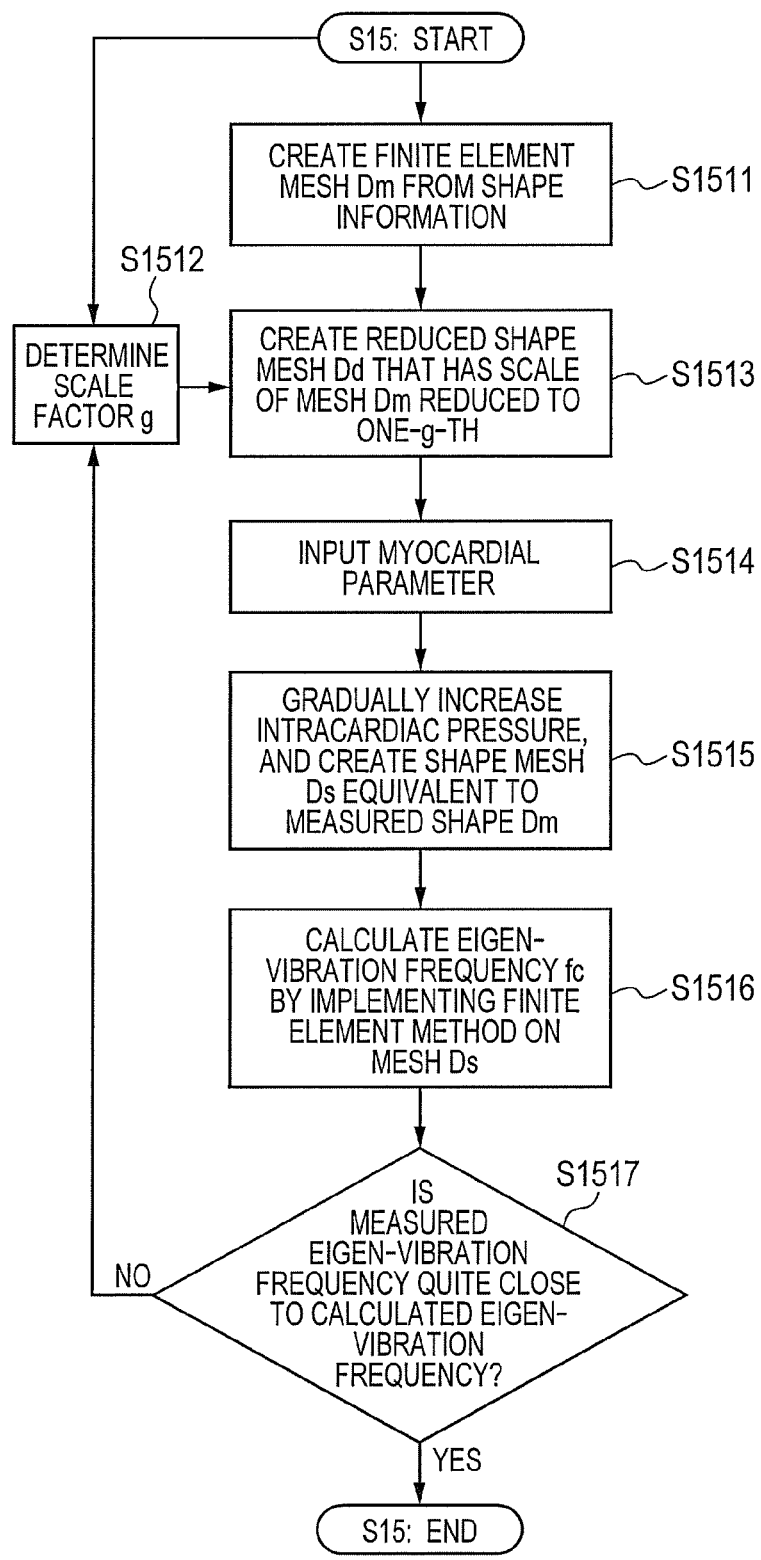
(a)
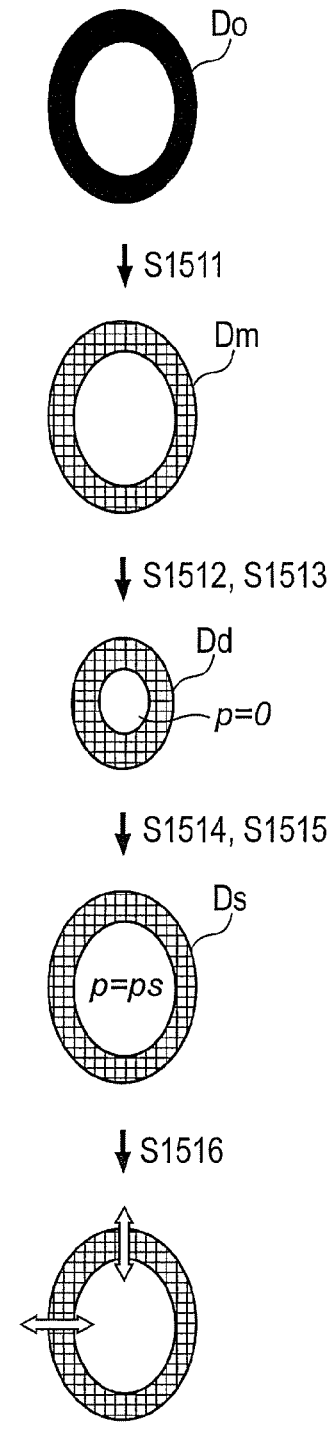
(b)

FIG. 8
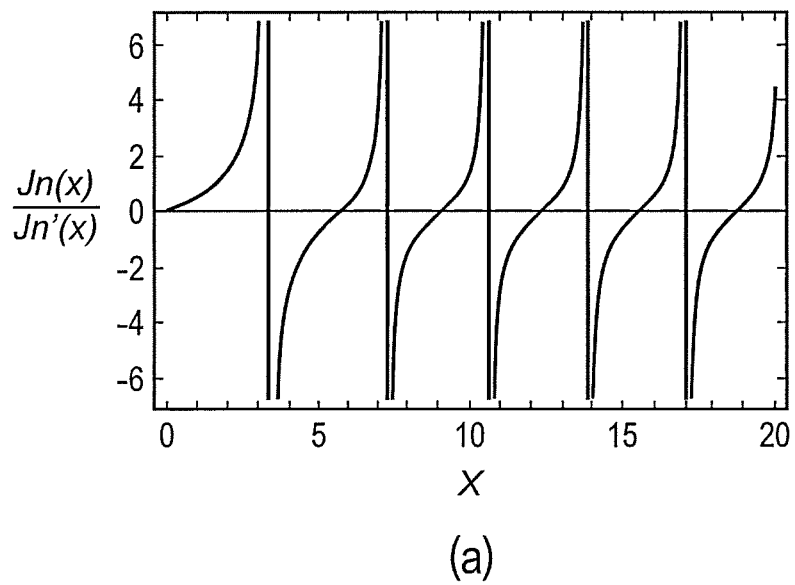
(a)
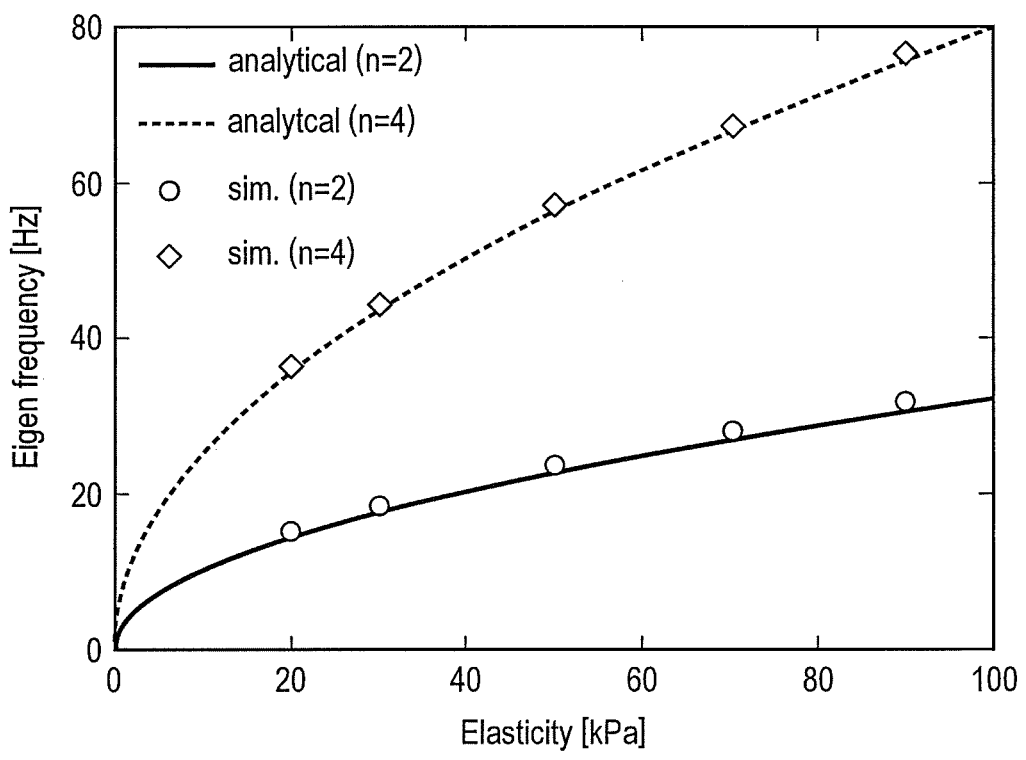
(b)

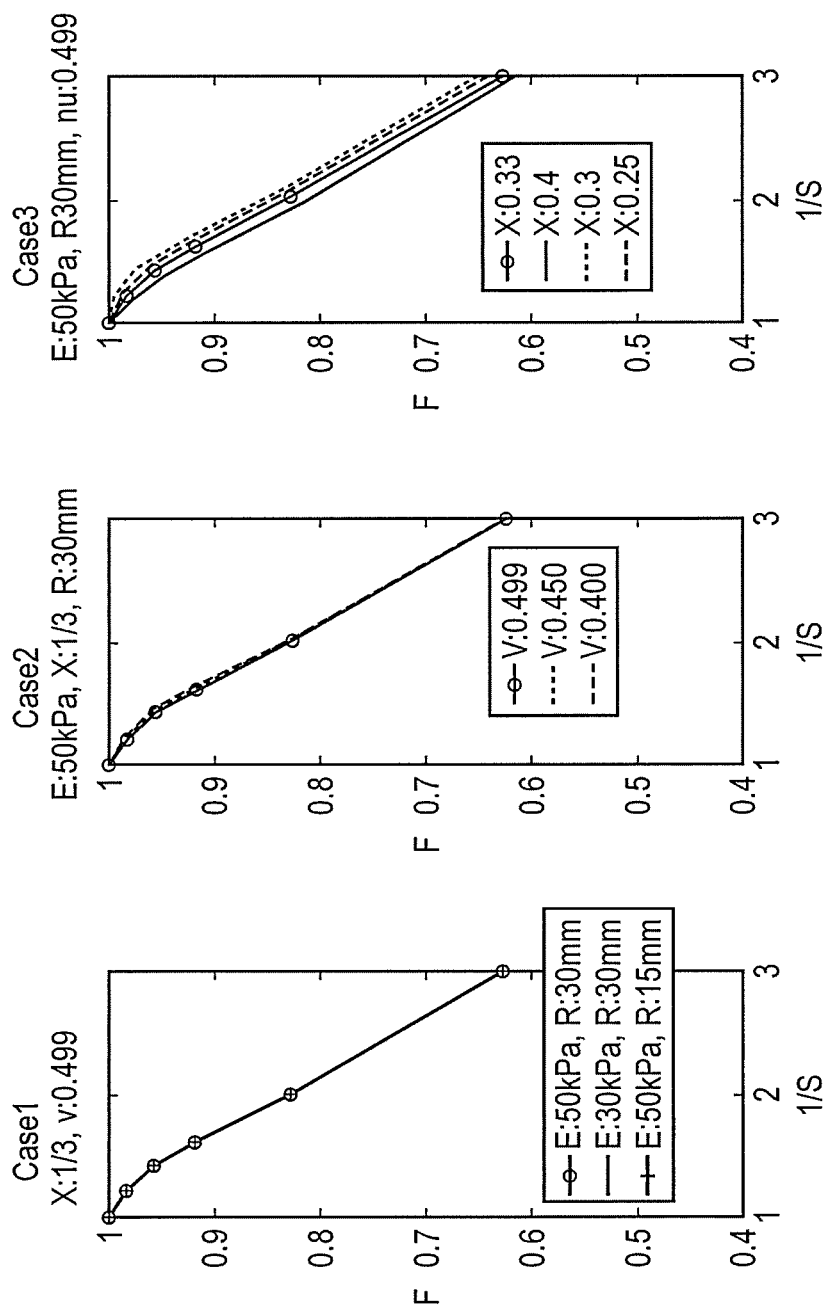

FIG. 9D mode 2X

| X \ 1/s | 0.25 | 0.30 | 0.33 | 0.40 |
|---|---|---|---|---|
| 1.0 | 1.00 | 1.00 | 1.00 | 1.00 |
| 1.2 | 0.88 | 0.88 | 0.89 | 0.90 |
| 1.4 | 0.77 | 0.79 | 0.80 | 0.82 |
| 1.6 | 0.69 | 0.71 | 0.72 | 0.75 |
| 2.0 | 0.57 | 0.60 | 0.62 | 0.66 |
| 3.0 | 0.45 | 0.49 | 0.52 | 0.56 | mode 2R

| X \ 1/s | 0.25 | 0.30 | 0.33 | 0.40 |
|---|---|---|---|---|
| 1.0 | 1.00 | 1.00 | 1.00 | 1.00 |
| 1.2 | 1.00 | 0.99 | 0.98 | 0.97 |
| 1.4 | 0.98 | 0.97 | 0.96 | 0.94 |
| 1.6 | 0.94 | 0.93 | 0.92 | 0.90 |
| 2.0 | 0.85 | 0.84 | 0.83 | 0.81 |
| 3.0 | 0.64 | 0.63 | 0.63 | 0.61 |

FIG. 9E mode 2X

| X  1/s | 0.25 | 0.30 | 0.33 | 0.40 |
|---|---|---|---|---|
| 1.0 | 0.090 | 0.097 | 0.102 | 0.110 |
| 1.2 | 0.079 | 0.086 | 0.091 | 0.099 |
| 1.4 | 0.069 | 0.076 | 0.081 | 0.090 |
| 1.6 | 0.062 | 0.069 | 0.074 | 0.083 |
| 2.0 | 0.051 | 0.059 | 0.064 | 0.073 |
| 3.0 | 0.041 | 0.048 | 0.053 | 0.062 | ized
ULTRASONIC IMAGING DEVICE AND INFORMATION PROCESSING DEVICE

TECHNICAL FIELD

The present invention relates to an ultrasonic imaging device for medical use, or more particularly, to an ultrasonic imaging technology for measuring the stiffness of the heart, which is desired by an examining person, or the blood pressure inside the heart.

BACKGROUND ART

Cardiac diseases are one of three major causes of death in many advanced countries. For early-stage diagnosis or progress observation of the cardiac diseases, temporal pressure information on the left atrium or left ventricle is used as an index directly useful in diagnosis. What is referred to as the pressure information on the inside of the heart refers to a differential pressure with respect to an atmospheric pressure and shall be called an intracardiac pressure.

For measuring the intracardiac pressure, an invasive method of inserting a cardiac catheter into the inside of a body is adopted. Information acquired by the catheter includes mainly a blood pressure in the aorta or left ventricle.

As a technology relating to noninvasive cardiac pressure measurement, a technique of inferring the stiffness of the cardiac muscle from an eigen-vibration frequency of the left ventricle, and measuring an intracardiac pressure has been devised. A method described in Non-patent Literature 2 is a technique that approximates the left ventricle to a spherical shell, and estimates the stiffness of the cardiac muscle using a relational expression of an eigen-vibration frequency of the spherical shell, which is filled with a fluid, and the stiffness thereof which is introduced in Non-patent literature 1. When the cardiac muscle is stiff, the eigen-vibration frequency increases. For example, when the intracardiac pressure is high, the myocardial tissue gets tensed, and the eigen-vibration frequency of a heart chamber increases. Further, N-patent Literature 3 makes a proposal on a technique of estimating the intracardiac pressure using a relational expression of the stiffness of the cardiac muscle and the intracardiac pressure which is introduced in Non-patent Literature 4.

CITATION LIST

Patent Literature

Patent literature 1: Japanese Patent Application Laid-Open Publication No. 10-5226

Non Patent Literature

Non-patent Literature 1: "Journal of Sound and Vibration (12(4), 453-463, 1970)" by S. H. Advani and Y. C. Lee, J.
Non-patent Literature 2: "American Journal of Physiology—Heart and Circulatory Physiology (266, H881-H890, 1994)" by H. Honda et al.
Non-patent literature 3: "Electronic Letters (32(11), 949-950, 1996)" by M. Sato et al.
Non-patent Literature 4: "Cardiac Mechanics (chapter 11, 1974)" by I. Mirsky and W. W. Parmley

SUMMARY OF INVENTION

Technical Problem

When a cardiac catheter is employed, an intracardiac pressure can be measured. However, since the measurement is invasive, a burden a patient incurs is quite heavy. In addition, as described in the related literature, when the left ventricle is approximated to a spherical shell in order to calculate the stiffness of the cardiac muscle or the intracardiac pressure from an eigen-vibration frequency, an obtained value and an error due to shape dependence are on the order of the same value, and lack precision.

An object of the present invention is to provide an ultrasonic imaging device and information processing device capable of noninvasively and highly precisely measuring a myocardial stiffness and an absolute pressure inside the heart.

Solution to Problem

In order to accomplish the foregoing object, according to the present invention, there is provided an ultrasonic imaging device including an ultrasonic probe that transmits or receives ultrasonic waves to or from the heart which is an object, a signal processing unit that processes a reflected echo signal received by the ultrasonic probe, and a display unit that displays the results of signal processing performed by the signal processing unit. The signal processing unit includes a shape extraction block that extracts shape information on the heart from the reflected echo signal, an eigen-vibration detection block that detects an eigen-vibration of the heart from the reflected echo signal, and an arithmetic block that calculates a myocardial stiffness or an intracardiac pressure from the obtained shape information and eigen-vibration.

In order to accomplish the aforesaid object, according to the present invention, there is provided an information processing device that processes a reflected echo signal obtained by transmitting or receiving ultrasonic waves to or from the heart, and that includes a signal processing unit which processes the reflected echo signal, and a display unit which displays the results of processing performed by the signal processing unit. The signal processing unit includes a shape extraction block that extracts shape information on the heart from the reflected echo signal, an eigen-vibration detection block that detects an eigen-vibration of the heart from the reflected echo signal, and an arithmetic block that calculates a myocardial stiffness or intracardiac pressure of the heart from the obtained shape information and eigen-vibration.

Advantageous Effects of Invention

According to the present invention, a myocardial stiffness and intracardiac pressure that are effective in diagnosis can be highly precisely provided by taking account of shape information on the heart that is an object of imaging.

In the present invention, since the laws of physics that take account of a geometric effect from an eigen-vibration frequency of the heart are used to noninvasively measure the shape of the heart and a motion thereof according to an ultrasonic image signal, a myocardial stiffness can be highly precisely calculated. Further, based on the obtained myocardial stiffness, an intracardiac pressure can be calculated using a relational expression of the stiffness of the heart and the pressure of the heart.

BRIEF DESCRIPTION OF DRAWINGS

FIG. 4 is a diagram for explaining a palmic time phase of the heart which relates to the first example.

FIG. 5 is a diagram for explaining a vibration of a cardiac wall in an end diastole which relates to the first example.

FIG. 6 is a diagram for explaining an ellipsoidal body and a vibration mode of the ellipsoidal body which relates to the first example.

FIG. 7 is a diagram for explaining detailed actions of the signal processing unit which relates to the first example.

FIG. 8 is an explanatory diagram of a function based on a spherical Bessel function which relates to a second example.

FIG. 9B is an explanatory diagram (2) showing the vibration frequency ratio between the spherical shell and ellipsoidal shell and relating to the second example.

FIG. 9D is a diagram showing an example of tables of vibration frequency ratios and relating to the second example.

FIG. 9E is a diagram showing an example of a table of non-dimensional parameters and relating to the second example.

DESCRIPTION OF EMBODIMENTS

Figure 1:
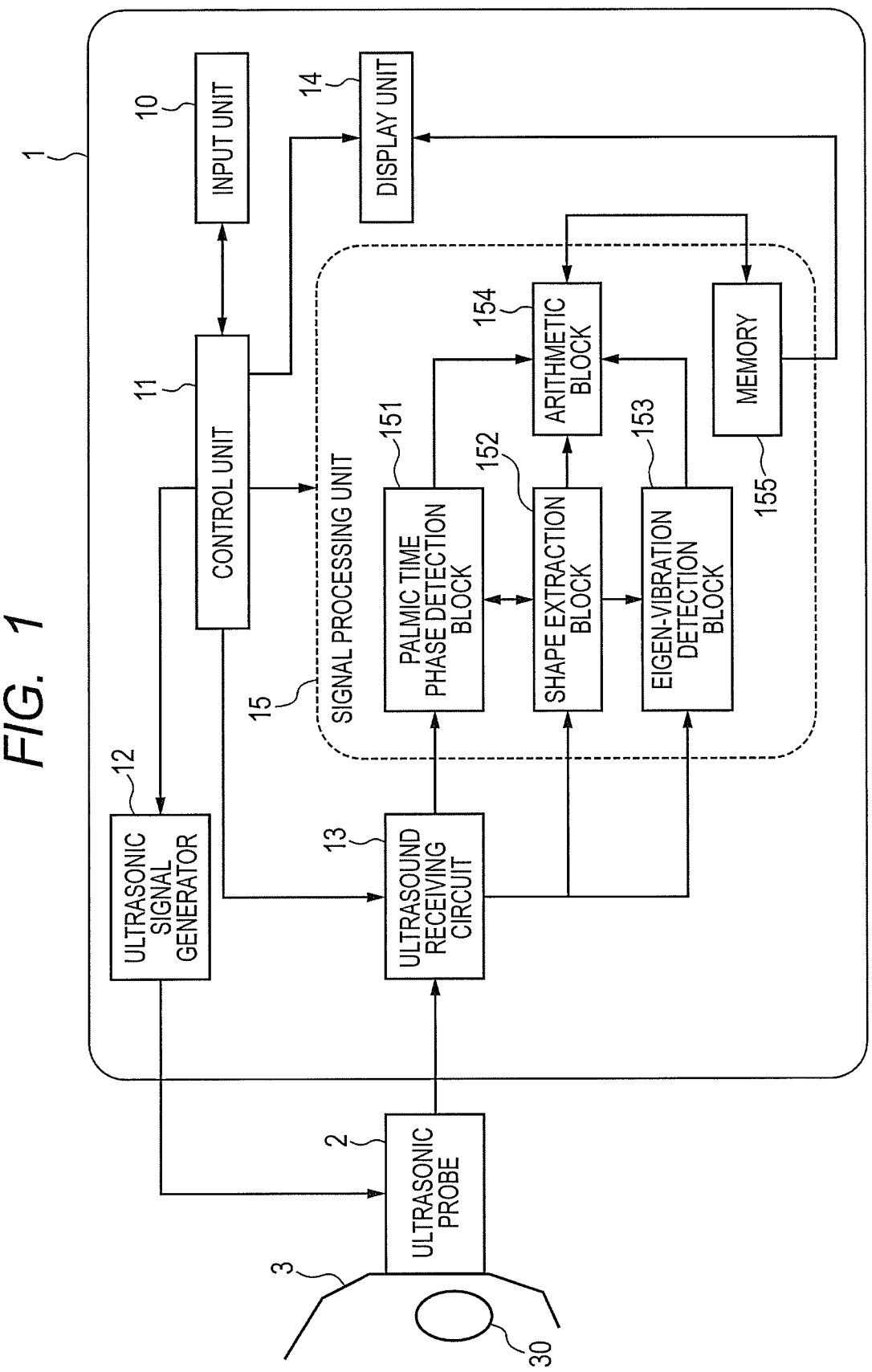
FIG. 1 is a block diagram showing an example of the configuration of an ultrasonic imaging device of a first example.

Referring to the drawings, various examples that are embodiments of the present invention will be described below.

EXAMPLE 1

To begin with, as the first example, an ultrasonic imaging device that processes a reflected echo signal using the finite element method will be described below. Specifically, a description will be made of the configuration of the ultrasonic imaging device that images an object using ultrasonic waves, and that includes an ultrasonic probe which transmits or receives ultrasonic waves to or from the heart that is the object, a signal processing unit which processes the reflected echo signal received by the ultrasonic probe, and a display unit which displays the results of signal processing performed by the signal processing unit. The signal processing unit includes a shape extracting block that extracts shape information on the heart from the reflected echo signal, an eigen-vibration detection block that detects an eigen-vibration of the heat from the reflected echo signal, and an arithmetic block that calculates a myocardial stiffness or intracardiac pressure of the heart on the basis of the shape information and eigen-vibration.

FIG. 1 is a block diagram showing an example of the configuration of the ultrasonic imaging device of Example 1. The ultrasonic imaging device includes a main body 1 and an ultrasonic probe 2.

The main body 1 is what produces an ultrasonic image while controlling the ultrasonic probe 2. The ultrasonic probe 2 is brought into contact with a subject 3 such as a living body according to a signal produced by an ultrasonic signal generator 12, irradiates ultrasonic waves to a region of irradiation 30, and receives a reflected echo signal of the region of irradiation 30.

Next, detailed components of the main body 1 will be described below. The main body 1 includes an input unit 10, a control unit 11, the ultrasonic signal generator 12, an ultrasound receiving circuit 13, a display unit 14, and a signal processing unit 15. The input unit 10 is a keyboard or pointing device with which an examining person who operates the ultrasonic imaging device sets operating conditions for the ultrasonic imaging device in the control unit 11, or an electrocardiogram signal input unit to be used in a case where an electrocardiogram is employed. The control unit 11 controls the ultrasonic signal generator 12, ultrasound receiving circuit 13, display unit 14, and signal processing unit 15 on the basis of the operating conditions for the ultrasonic imaging device set with the input unit 10, and is constructed as, for example, a sequencer or program run in a central processing unit (CPU) included in a processing unit of a computer system. The ultrasound receiving circuit 13 amplifies or phases a reflected echo signal received by the ultrasonic probe 2, and inputs the resultant signal to the signal processing unit 15. The display unit 14 outputs image information, which is provided by the signal processing unit, or a myocardial stiffness or intracardiac pressure and the like, which will be described later, onto a display. The signal processing unit 15 has the capability to produce an ultrasonic image on the basis of the reflected echo signal sent from the ultrasound receiving circuit 13, that is, the ultrasonic probe 2.

Next, detailed components of the signal processing unit 15 will be described below. The signal processing unit 15 includes a palmic time phase detection block 151, shape extraction block 152, eigen-vibration detection block 153, arithmetic block 154, and a memory 155 that is a memory block. Incidentally, the palmic time phase detection block 151, shape extraction block 152, and eigen-vibration detection block 153, and arithmetic block 154, which are the functional blocks of the signal processing unit 15, are realized with program runs in the CPU. The palmic time phase detection block 151 detects the velocity or direction of a bloodstream through a cardiac valve on the basis of an input signal, reflected echo signal, or shape information fetched from the input unit 10, acquires the systolic or diastolic time phase of the heart, and thus recognizes a palmic time phase. Otherwise, the palmic time phase detection block 151 detects the palmic time phase on the basis of the shape information provided by the shape extraction block 152.

The shape extraction block 152 forms, according to a reflected echo signal outputted from the ultrasound receiving circuit 13, a two-dimensional tissular shape, which has the heart as a center, using, for example, a Brightness (B) mode, that is, planar imaging method for an object of ultrasound irradiation, or a three-dimensional tissular shape using a stereoscopic imaging method.

The eigen-vibration detection block 153 measures an eigen-vibration of a tissue provided by the shape extraction block 512. The arithmetic block 154 calculates the stiffness of the tissue from the shape information and eigen-vibration information on the tissue using the finite element method. The memory 155 stores, in addition to, reflected echo signal data, data, which is processed by the palmic time phase detection block 151, shape extraction block 152, eigen-vibration detection block 153, or arithmetic block 154, and resultant data. Needless to say, the memory 155 may be installed outside the signal processing unit 15.

Figure 2:
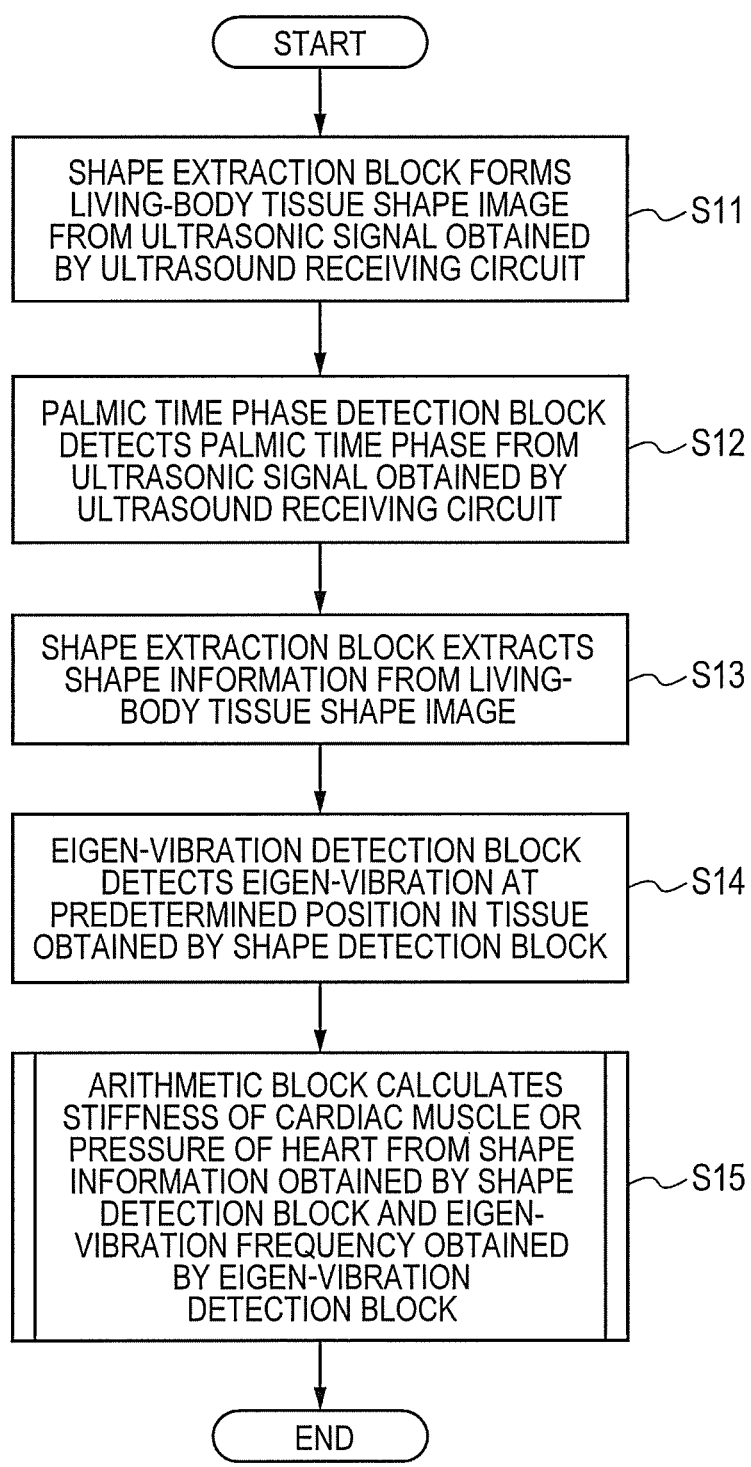
FIG. 2 is a flowchart presenting an example of actions of a signal processing unit and relating to the first example.

FIG. 2 presents a processing flow of the device of the present example, or more particularly, of the signal processing unit 15. In FIG. 2, as a concrete example, the region of irradiation 30 in FIG. 1 is a region including the left ventricle of the heart, but the region of irradiation 30 may be the left atrium, right atrium, or right ventricle.

First, the shape extraction block 152 forms, according to a reflected echo signal outputted from the ultrasound receiving circuit 13, for example, a B-mode image, that is, a two-dimensional shape image of the left ventricle based on a planar imaging method for an object of ultrasound irradiation, or a three-dimensional shape image of the left ventricle based on a stereoscopic imaging method (S11), and transmits the tissular shape image to the palmic time phase detection block 151. The palmic time phase detection block 151 detects a palmic time phase on the basis of the reflected echo signal or shape information sent from the ultrasound receiving circuit 13, or information fetched from the input unit 10 (S12), and transmits the palmic time phase information to the shape extraction block 152. Thereafter, the shape extraction block 152 determines information on a position, at which the tissue in each image is located, from brightness information of the tissular shape image using image processing, extracts shape information on the left ventricle in a predetermined time phase (S13), and transmits the shape information to the eigen-vibration detection block 153.

Thereafter, the eigen-vibration detection block 153 detects an eigen-vibration at a predetermined point in the shape information (S14), and transmits the eigen-vibration information to the arithmetic block 154. Finally, the arithmetic block 154 calculates stiffness information on the left ventricle or information on an intracardiac pressure, which is a pressure inside the heart, from the shape information on the left ventricle and eigen-vibration information. When step 12 is executed, if the shape information acquired at step 11 is left unused, the sequence of step 11 and step 12 may be reversed, or step 11 and step 12 may be executed concurrently. The sequence of step 13 and step 14 may be reversed, or step 13 and step 14 may be executed concurrently.

Figure 3:
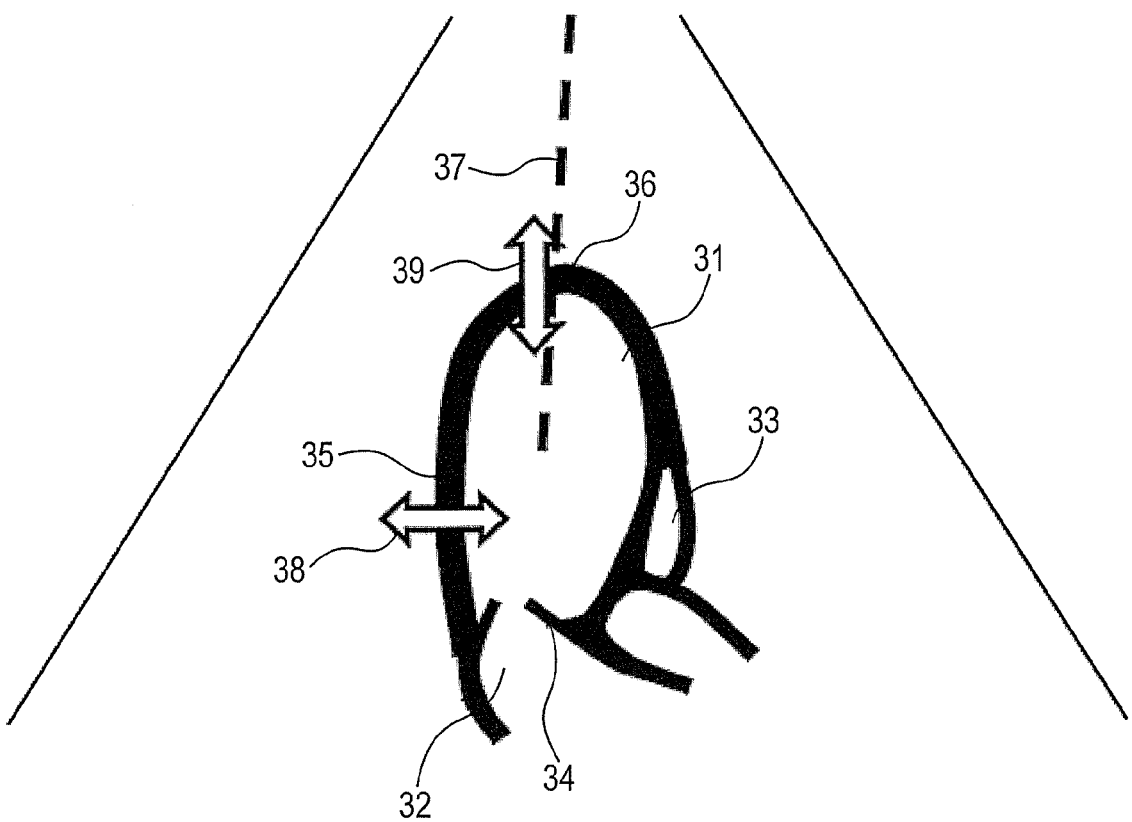
FIG. 3 is a diagram showing a B-mode image for explaining a vibration of the heart and relating to the first example.

Referring to FIG. 3, an example of shape information on the heart, which is an object, obtained at step 11 will be described below. FIG. 3 shows the left ventricle 31 of the heart, left atrium 32, right ventricle 33, mitral valve 34, posterior wall 35 of the left ventricle, and apex cordis 36 which are imaged in a two-dimensional B-mode. The explanatory diagram is a two-dimensional image, but a three-dimensional image will do. The ultrasonic frequency for the B-mode image may fall within the range from 1 MHz to 20 MHz which permits imaging. In the present example, the center frequency is 5 MHz. A pulse repetition frequency (PRF) for imaging the heart shall fall within a range of 20 Hz or higher, that is, a range within which a motion of the heart can be caught.

An example of a palmic time phase detection method at step 12 will be described below in conjunction with FIG. 4.

FIG. 4 shows changes in time-sequential physical quantities in a palmic time phase, for example, changes in an electrocardiogram signal waveform 61, mitral valve inflow velocity waveform 62, pulmonary-artery valve regurgitation waveform 63, cardiac-wall velocity waveform 64, and cardiac-wall motion waveform 65. When an electrocardiogram signal is employed, a palmic time phase derived from the electrocardiogram signal waveform 61 fetched from the input unit 10 can be recognized. An electrocardiogram characteristically shows the palmic time phase. The electrocardiogram may be unemployed. When any of the physical quantities 62 to 65 in FIG. 4 which exhibit a characteristic change along with a change in the electrocardiogram time phase can be used, if a maximum value, minimum value, the largest value, the smallest value, a slope, a zero-crossing, or the like is employed, the time phase can be detected. As a waveform acquisition method, for example, the mitral valve inflow velocity waveform 62 of a bloodstream passing through the mitral valve 34 is measured by measuring a Doppler signal. Thus, the palmic time phase can be recognized. In addition, a bloodstream waveform may be the pulmonary-artery valve regurgitation waveform 63, a velocity waveform of a bloodstream passing through the aortic valve or tricuspid valve, the cardiac wall velocity waveform 64, or the cardiac wall motion waveform 65 obtained by time-sequentially measuring a movement of the cardiac wall in a motion (M) mode. Otherwise, a waveform that time-sequentially expresses a vibration detected by the eigen-vibration detection block 153 will do. Anyway, the palmic time phase detection block 151 can recognize the palmic time phase from any of the waveforms.

In the present example, a time phase of an end diastole 66 which is useful in diagnosis is especially noted. The end diastole 66 is a time phase in which the left ventricle 31 is filled with blood and which immediately precedes a time phase in which blood is pumped out. A time phase in which the volume of the left ventricle is maximized may be detected. Herein, what is referred to as a B-mode image is an image expressing a tissular shape imaged with ultrasonic waves. What is referred to as an M-mode image is an image time-sequentially expressing a motion of a tissue by temporally tracking the motion of the tissue on an arbitrary ultrasonic scanning line and by marking the position of the tissue on the scanning line on the axis of ordinates and time on the axis of abscissas.

At step 13 in FIG. 2, positional information on a tissue image obtained at step 11 is detected through image processing. More particularly, since a tissue is detected as a high luminance value in an ultrasonic image, a high-luminance value portion is regarded as a cardiac tissue and a two-dimensional or three-dimensional cardiac-tissue position is acquired.

At step 14, the eigen-vibration detection block 153 uses a reflected echo signal, which is outputted from the ultrasound receiving circuit 13, to measure an eigen-vibration frequency at a predetermined position in a tissue image obtained at step 11. The predetermined position may be selected from the tissue image by a user, or may be determined according to an instruction from the input unit 10. Otherwise, the characteristic posterior wall 35 of the left ventricle or apex cordis 36 may be determined through image processing to be performed on by the signal processing unit 15. In the present example, a PRF in the M mode in which the eigen-vibration frequency ranging from 10 Hz to 100 Hz is calculated shall be equal to or higher than 200 Hz.

Step 14 will be detailed in conjunction with FIG. 3 and FIG. 5. A position at which an eigen-vibration is detected may be any position on the wall of a heart chamber that is an object. In the present example, the object is the left ventricle. Therefore, detection of an eigen-vibration at the apex cordis 36 shown in FIG. 3 will be described as an example. As for an eigen-vibration frequency detection method, a means using the M mode will be described.

FIG. 5 shows an M-mode image obtained using the ultrasonic scanning line 37 that encompasses a detection point and is shown in FIG. 3. In the M mode, an eigen-vibration in the end diastole 66 can be detected by time-sequentially observing the oscillation of the cardiac-wall motion waveform 65 representing a motion of the cardiac wall. In the present example, the eigen-vibration in the time phase of the end diastole 66 which is useful in diagnosis and in which the heart is relaxed is noted. A wall vibration in the end diastole 66 is subjected to spectrum analysis, whereby the eigen-vibration frequency 39 at the apex cordis 36 can be calculated. The spectrum analysis may be Fourier transform or wavelet transform. The number of eigen-vibration frequencies to be measured is one or more. When plural eigen-vibration frequencies are measured, in addition to the eigen-vibration frequency 39, an eigen-vibration frequency 38 on the posterior wall 35 of the left ventricle and an eigen-vibration frequency in any other place may be measured.

Referring to FIG. 6, a relationship between an eigen-vibration and a place of measurement will be described. Numerous eigen-vibration modes of a shell are present. Depending on a way of vibration in each of the eigen-vibration modes, a place where a vibration is marked and a place where a vibration is little are observed. Referring to FIG. 6, a description will be made by taking a vibration of an ellipsoidal shell for instance. In part (a) of FIG. 6, an ellipsoidal shell 67 is present in a polar coordinate system expressed with an axial direction x, radial direction r, and circumferential direction θ. A vibration in a mode 2x of the x-axis direction on an xr plane 671 is shown in part (b) of FIG. 6, and a vibration in a mode 2r of the r direction on an rθ plane 672 is shown in part (c) of FIG. 6. Typical deformed states 675 and 676 express opposite phases of vibrations.

The vibration modes in parts (b) and (c) of FIG. 6 are different from each other, and eigen-vibration frequencies are different from each other accordingly. Since a vibration is measured at plural positions, modes characteristic of the various vibration modes can be grasped. For example, at a point of measurement 673, a vibration in the mode 2x can be markedly measured, but a vibration in the mode 2r is hardly detected. In contrast, at a point of measurement 674, eigen-vibration frequencies in both the modes 2x and 2r can be measured. Namely, when the number of points of measurements is one, it is hard to identify a mode. By measuring plural points, a mode can be identified.

At step 15 in FIG. 2, the arithmetic block 154 calculates a tissular stiffness from shape information and eigen-vibration information on a tissue using the finite element method. In particular, when the finite element method is implemented, two important physical quantities, that is, a myocardial stiffness E [Pa] and intracardiac pressure p [Pa] are unknown. In order to determine the physical quantities, a repetition method is employed in the present example.

Referring to FIG. 7, detailed processing of the finite element method in the present example will be described below. Part (a) of FIG. 7 shows the detailed flow, while part (b) of FIG. 7 shows schematic diagrams in line with the flow. The arithmetic block 154 creates a finite element mesh Dm from shape information Do extracted by the shape detection block 152 (S1511). Herein, since a pressure is applied to the inside of the heart, the cardiac muscle is stretched and the heart chamber is dilated. A state in which the heart is wilted with no pressure applied is inferred from the mesh Dm. The wilted state is inferred using a scaling factor g.

The scaling factor g denotes a value ranging from 0 to 1 and is determined arbitrarily at the time of arithmetic (S1512). By reducing the scale of the mesh information Dm to a one-g-th, mesh information Dd in the wilted state is calculated (S1513). Herein, the scale is reduced so that the mass of a myocardial tissue is held intact. For example, the diameter of the cardiac wall may be diminished, and the wall thickness may be increased. At this time, the intracardiac pressure is equivalent to an external pressure. A reference pressure of the intracardiac pressure in the present example is the atmospheric pressure, an indication of the intracardiac pressure is a differential pressure from the atmospheric pressure. Namely, the intracardiac pressure of the wilted cardiac mesh Dd calculated at step 1513 is 0 mmHg. Thereafter, parameters for the finite element method are determined. Physical properties are set to ranges within which diagnostic effectiveness is maintained. Namely, a myocardial density is set to a constant ranging from 950 kg/m$^3$ to 1150 kg/m$^3$, and a blood density is set to a constant ranging from 950 kg/m$^3$ to 1150 kg/m$^3$. As for a myocardial stiffness E, a relational expression of formula (1) (Non-patent Literature 4) is employed (S1514).

$$E = k_1 \sigma + k_2 \quad \text{(formula 1)}$$

where σ denotes a stress of the left-ventricle wall in a wall to thickness direction [Pa], and k1 (no unit) and k2 [gm/mm$^2$] denote constants concerning elasticity. Specifically, k1 is known to range from 29.9 to 43.7, and an experimental mean value is 37.3 (Non-patent Literature 4), and k$_2$ denotes a constant ranging from 0 to −2.13 [gm/mm$^2$].

Thereafter, the finite element method is used to gradually increase the intracardiac pressure of the mesh Dd so as to gradually dilate the mesh Ds. The mesh Dd is dilated to have substantially the same size as the measured mesh information Dm (S1515). The dilated mesh information shall be mesh information Ds, and the intracardiac pressure at this time shall be an intracardiac pressure p. Thereafter, the mesh information Ds is used to calculate an eigen-vibration frequency f$_c$ (S1516). The calculated eigen-vibration frequency f$_c$ is compared with a measured eigen-vibration frequency fm (S1517). If both the eigen-vibration frequencies are very close to each other, a finite element model satisfactorily reflects the measured heart, and the stiffness E and pressure p employed in the calculation are adopted as an actual stiffness and intracardiac pressure.

If the eigen-vibration frequency f$_c$ is different from the measured vibration frequency f$_m$, the scale factor g is changed and steps 1512 to 1517 are repeated. A decision that the eigen-vibration frequency f$_c$ is satisfactorily close to the measured vibration frequency fm may be made when, for example, an error between the frequencies falls below a certain threshold. The threshold may be 15% or less that is a permissible error. The scaling factor g may be exhaustively changed, and the scaling factor g minimizing an error between the eigen-vibration frequency fc and measured vibration frequency fm may be selected. According to the foregoing present example, the stiffness E of the heart that is an object of imaging or the pressure p thereof can be calculated.

Next, a display image on the display unit of the ultrasonic imaging device of the present example will be detailed below. The display unit 14 in FIG. 1 displays, on the screen thereof, an intracardiac pressure at one or more spatial positions, at a certain time, or at one or more of successive times, which is calculated by the arithmetic block 154 of the signal processing unit 15, a vibration frequency, spectrum analysis of the vibration frequency, a magnitude of movement of a wall surface, or the stiffness of the heart. The spectrum analysis may be short-term Fourier transform or wavelet analysis making it possible to detect a frequency dependent on a time phase. A spectrum analysis diagram is a contour diagram having two axes one of which indicates time and the other of which indicates a frequency. Spectral intensities may be expressed in colors.

Figure 12:
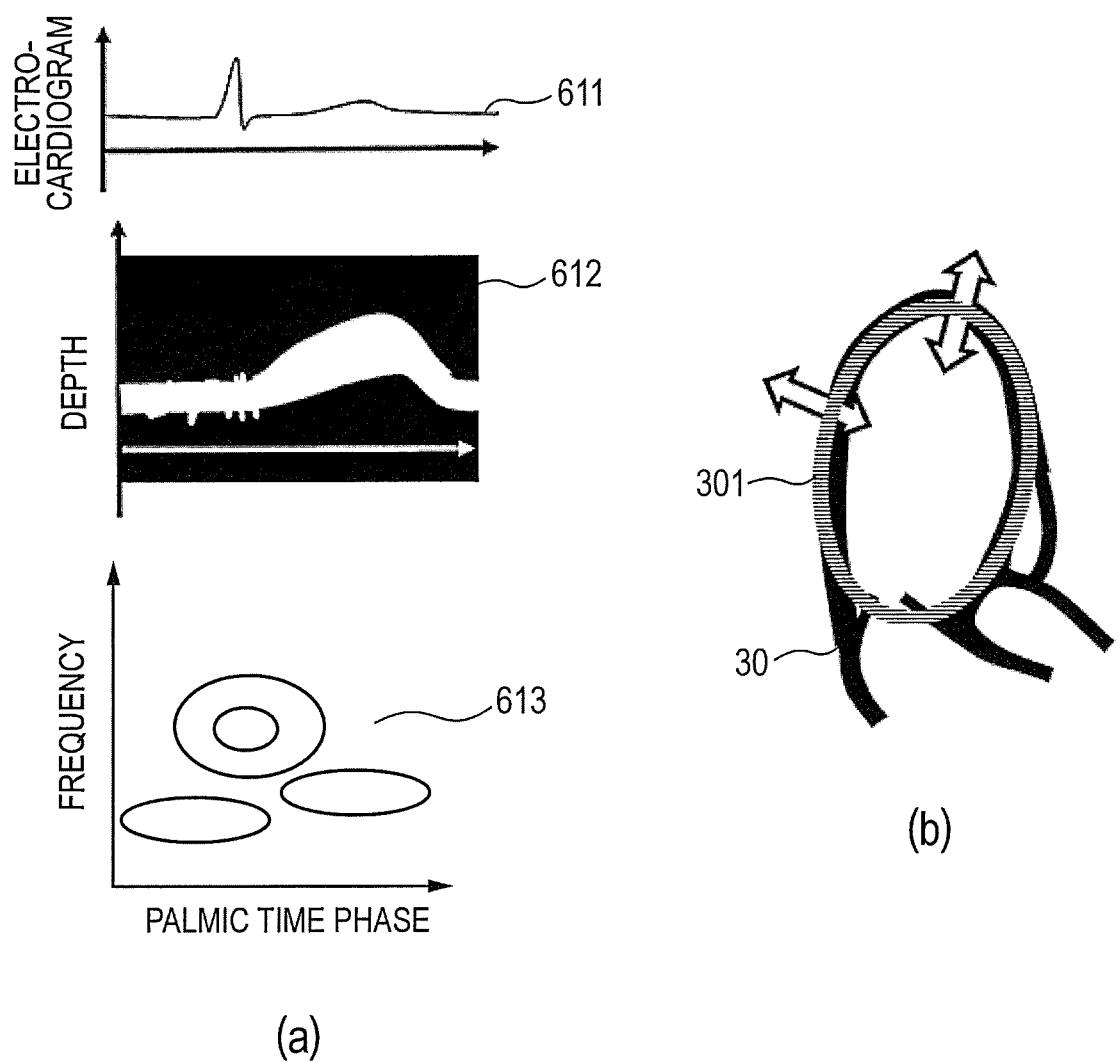
FIG. 12 is a diagram showing an example of screen display and relating to the examples.

As an example, the lowest part (a) of FIG. 12 shows a spectrum analysis diagram 613 derived from short-term Fourier transform. One of axes may indicate a frequency, and the other one thereof may indicate a spectral intensity. As shown in part (a) of FIG. 12, an electrocardiogram 611 showing a time phase, an M-mode display diagram 612, and the spectrum analysis diagram 613 derived from Fourier transform or the like may be displayed on the same screen. A tissue image 30 shown in part (b) of FIG. 12 may be superposed on an image, which is formed by the shape extraction block 152, on the same screen. Further, a vibration mode may be indicated with a motion picture or still image. As shown in part (b) of FIG. 12, when ellipsoidal body approximation of step 13 in the second example to be described later is carried out, a cardiac tissue and ellipsoidal body 301 may be displayed while being superposed on each other.

EXAMPLE 2

Next, an ultrasonic imaging device of the second example will be described below. In the first example, the finite element method is used to calculate a myocardial stiffness or intracardiac pressure. In the second example, the finite element method is not used, but a heart chamber is approximated to an ellipsoidal shell and the laws of physics concerning the ellipsoidal shell and eigen-vibration frequency are employed. The ultrasonic imaging device of the present example has the same configuration as the device shown in FIG. 1 and described as Example 1. A difference lies in processing to be performed by the signal processing unit 15 of the device shown in FIG. 1. As described later, especially, the steps 13 and 15 of the processing flow described in FIG. 2 are different from those in Example 1.

Prior to details of the present example, a description will be made of the laws of physics concerning a spherical shell and eigen-vibration frequency and extension to the relationship between an ellipsoidal shell and eigen-vibration frequency. In the related art literatures, a dominant equation (Non-patent Literature 1) representing an eigen-vibration frequency of a spherical shell is introduced, but a relational expression of an ellipsoidal shell, which resembles an actual heart chamber, and an eigen-vibration frequency is unknown. Herein, a description will be made of a technique that uses the eigen-vibration frequency of the ellipsoidal shell to calculate the stiffness of the ellipsoidal shell in compliance with the law of the dominant equation representing the eigen-vibration frequency of the spherical shell.

A dominant equation representing an eigen-vibration frequency of a spherical shell is expressed by a formula (2) (Non-patent Literature 2). Herein, $\beta_n$ denotes a variable that is a dimensionless value of an eigen-vibration frequency fn. $C_{6a}$, $C_{4a}$, $C_{2a}$, $C_{0a}$, $C_{6b}$, $C_{4b}$, $C_{0b}$, $C_a$, and $C_b$ are nine constants determined with a ratio h/r of a wall thickness to an inner diameter which implies a shape, and a Poisson ratio $c_b$. $J_n(x)$ and $J_n'(x)$ denote a spherical Bessel function of the n-th kind of a variable x and its derivation.

$$C_{6a}\beta_n^6 + \left(C_{4a} + C_{4b}\frac{\beta_n}{E^{\frac{1}{2}}}\frac{J_n\left(C_a\beta_n E^{\frac{1}{2}}\right)}{J_n'\left(C_a\beta_n E^{\frac{1}{2}}\right)}\right)\beta_n^4 + \\ \left(C_{2a} + C_{2b}\frac{\beta_n}{E^{\frac{1}{2}}}\frac{J_n\left(C_a\beta_n E^{\frac{1}{2}}\right)}{J_n'\left(C_a\beta_n E^{\frac{1}{2}}\right)}\right)\beta_n^2 + \\ \left(C_{0a} + C_{0b}\frac{\beta_n}{E^{\frac{1}{2}}}\frac{J_n\left(C_a\beta_n E^{\frac{1}{2}}\right)}{J_n'\left(C_a\beta_n E^{\frac{1}{2}}\right)}\right) = 0 \quad \text{(formula 2)}$$

$$\beta_n = C_b \frac{f_n}{E^{1/2}} \quad \text{(formula 3)}$$

$$C_b = 2\pi r \rho^{1/2}(1-v^2)^{1/2}$$

While the formula (2) is complex and numerically solved, the function $J_n(x)/J_n'(x)$ varies, as shown in part (a) of FIG. 8, depending on the x value from a negative infinite to a positive infinite. The solution of $\beta_n$ meeting the formula (2) numerously exists. This poses a problem in that a value E cannot be uniquely determined.

In the present example, a unique solution can be obtained using an asymptotic approximate expression (4) to a zero point by utilizing the fact that an input part ($c_a\beta nE^{1/2}$) of a spherical Bessel function is so small as to be on the order of 0.001 in a vibration mode of the cardiac muscle.

$$\lim_{x \to 0} J_n(x) = \frac{x^n}{(2n+1)!!} \quad \text{(formula 4)}$$

$$n!! = n(n-2)(n-4)\ldots$$

When this relational expression is assigned to the formula (2), a formula below ensues.

$$\left(C_{6a} + \frac{C_{4b}C_a}{n}\right)\beta_n^6 + \\ \left(C_{4a} + \frac{C_{2b}C_a}{n}\right)\beta_n^4 + \left(C_{2a} + \frac{C_{0b}C_a}{n}\right)\beta_n^2 + C_{0a} = 0 \quad \text{(formula 5)}$$

The use of the asymptotic approximation has two merits. One of the merits is such that although the formula (2) includes two variables of $\beta_n$ and E, the formula (5) includes one variable of $\beta_n$ alone. Specifically, the formula (2) implies a possibility that the solution of $\beta_n$ may vary depending on the tissular stiffness E value. In the formula (5), when a spherical radius-vs.-wall thickness ratio and Poisson ratio are identical to each other, coefficients are identical to one another. Therefore, the $\beta n$ value is held unchanged irrespective of the tissular stiffness E value. Once a shape and the Poisson ratio are determined, the $\beta_n$ value is determined. This conclusion drawn out from a spherical shell implies a possibility that even when an ellipsoidal shell is employed, once a shape is determined, the $\beta_n$ value can be determined irrespective of the E value. The present inventor has extended the possibility, which once the shape is determined, the $\beta_n$ value can be determined irrespective of the E value, to the ellipsoidal shell. The extension will be described later.

The second merit lies in a point that since the formula (5) is a cubic equation of $\beta_n^2$, $\beta_n$ can be calculated into an analytical solution. This obviates the necessity of numerical repetitive calculation at the time of calculation of a myocardial stiffness E, and signifies that a calculation time can be shortened.

Part (b) of FIG. 8 shows an example of comparison of an analyzed analytical solution (analytical) with a numerical solution (simulation) obtained according to the finite element method. In the drawing, the axis of abscissas indicates a stiffness (Elasticity), and the axis of ordinates indicates an eigen-vibration frequency (Eigen frequency). A solid line and dot line each indicate the relationship of the eigen-vibration frequency based on the analytical solution to the stiffness, and express a mode 2 (n=2) and mode 4 (n=4) respectively. Round marks and diamond marks indicate results of calculation based on the finite element method, and express the mode 2 and mode 4 respectively. For both the mode 2 and mode 4, the analytical solution and numerical solution agree with each other. The validity of the solution of the formula (5) is demonstrated.

Next, extension of an eigen-vibration frequency of a spherical shell to an ellipsoidal body will be described below. Based on the aforesaid finding that the dimensionless value $\beta_n$ derived from an asymptotic approximation technique for the eigen-vibration frequency of the spherical shell and obtained from a myocardial stiffness and eigen-vibration frequency is determined with the shape of the shell and a Poisson ratio, it is suggested that even when the ellipsoidal shell is concerned, once the shape is determined, the value $\beta_n$ of the ellipsoidal shell is determined. In order to verify the suggestion, an eigen-vibration frequency ratio F between the ellipsoidal shell, which is filled with a fluid, and the spherical shell is calculated with a major-axis radius-vs.-minor-axis radius ratio s as a function according to the finite element method. A vibration mode is free vibration. Conditions for the calculation are that the densities of the fluid, with which the ellipsoidal shell is filled, and the tissue of the shell are 1000 kg/m³. The calculation is performed in three cases to be described below.

To begin with, in a case 1, in order to demonstrate that a vibration-frequency ratio F does not depend on a stiffness E or radius R, a spherical shell having a stiffness of 50 kPa and a radius of 30 mm, a spherical sell having a stiffness of 30 kPa and a radius of 30 mm, and a spherical shell having a stiffness of 50 kPa and a radius of 15 mm are compared with one another. A Poisson ratio is set to 0.499, and a ratio of a wall thickness to a spherical-shell radius is set to ⅓. In a case 2, in order to investigate an effect of the Poisson ratio $\upsilon$ on the vibration-frequency ratio F, the Poisson ratio $\upsilon$ is varied. In the case 2, the spherical shell having the stiffness of 50 kPa, the radius of 30 mm, and the ratio of the wall thickness to the spherical-shell radius of ⅓ is adopted as an object of calculation. In a case 3, in order to investigate an effect of the ratio of the wall thickness to the radius (X=h/r), the X value is varied. In the case 3, the spherical shell having the stiffness of 50 kPa, the radius of 30 mm, and the Poisson ratio of 0.499 is adopted as an object of calculation.

Figure 9A:
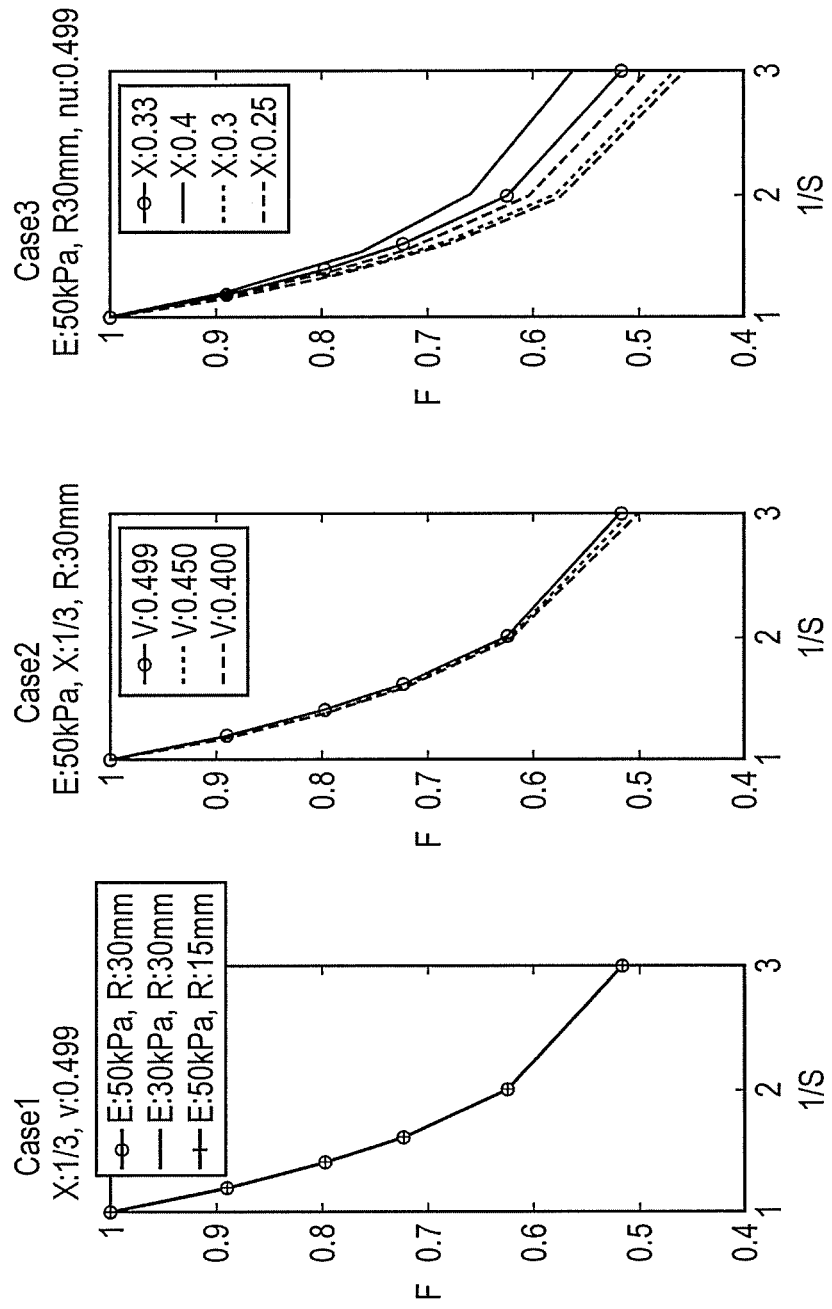
FIG. 9A is an explanatory diagram (1) showing a vibration frequency ratio between a spherical shell and ellipsoidal shell and relating to the second example.
Figure 9C:
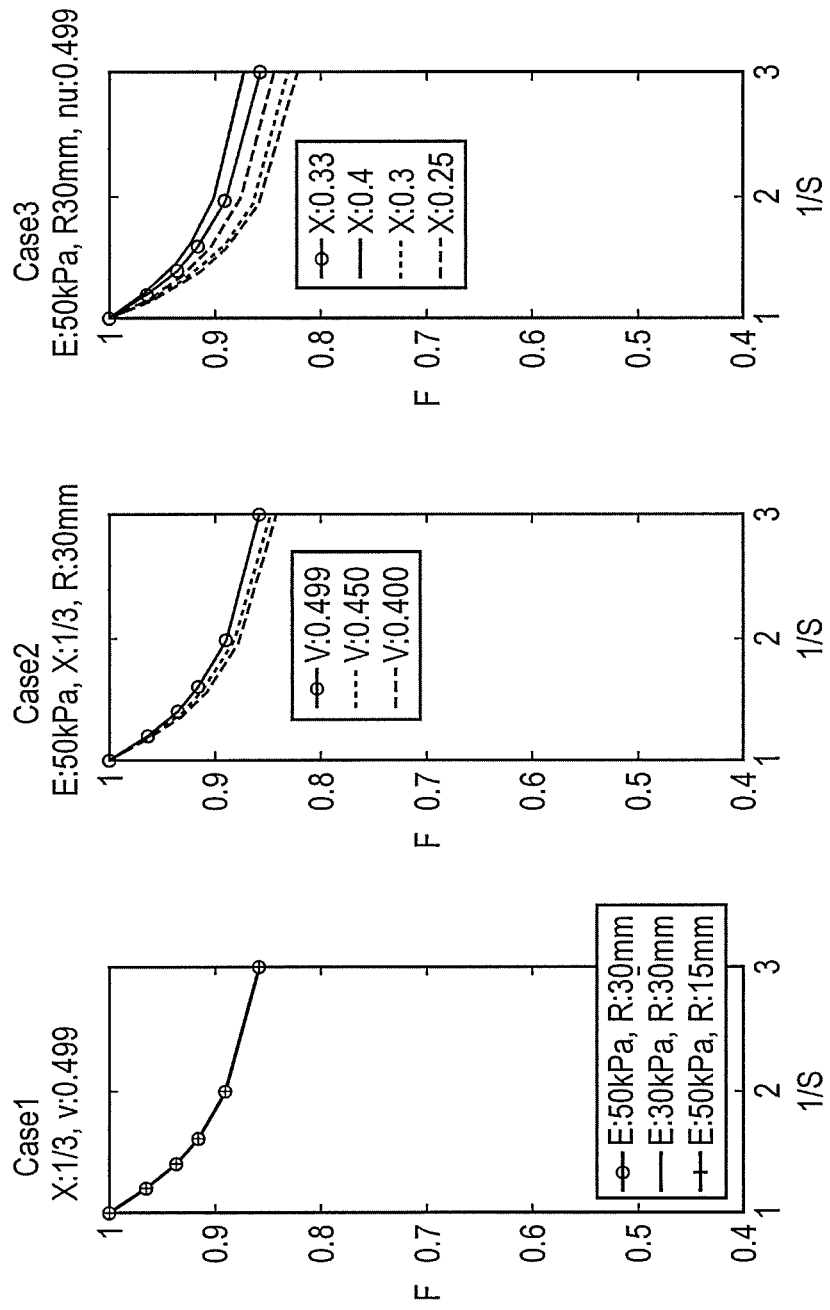
FIG. 9C is an explanatory diagram (3) showing the vibration frequency ratio between the spherical shell and ellipsoidal shell and relating to the second example.

FIG. 9A, FIG. 9B, and FIG. 9C each show an eigen-vibration frequency ratio F (axis of ordinates) between an ellipsoidal shell, which is filled with a fluid, and a spherical shell as a function of a major-axis radius-vs.-minor-axis radius ratio s (axis of abscissas) in relation to each of three cases 1, 2, and 3. Herein, the radius of the spherical body shall be equal to the minor-axis radius of the ellipsoidal body. FIG. 9A shows a mode 2R (n=2) on the rθ plane shown in FIG. 6, FIG. 9B shows a mode 2X (n=2) on the xr plane shown in FIG. 6, and FIG. 9C shows a mode 4R (n=4) on the rθ plane shown in FIG. 6.

When the major-axis radius-vs.-minor-axis radius ratio s takes on 1, the ellipsoidal body assumes a sphere, and the frequency ratio is 1. As the s value gets smaller, the ellipsoidal body frequency decreases. In the case of the mode 2R, when the major-axis radius-vs.-minor-axis radius ratio s takes on 0.5, that is, when the minor-axis radius is a half of the major-axis radius, the frequency of the ellipsoidal body is decreased down to about 60%. When the stiffness of the cardiac muscle is a square of the frequency, an effect is exerted. Therefore, assuming that the frequency of the ellipsoidal body is measured and the spherical body is treated, there is a possibility that a calculated stiffness may be estimated to be as low as several tens of percent of an actual stiffness. As for calculation in the case 1, the frequency ratios in the respective modes in FIG. 9A, FIG. 9B, and FIG. 9C are consistent with one another. This signifies that the frequency ratio does not depend on a size or stiffness. In the case 2, a slight effect of a Poisson ratio is observed, but the frequency ratios in all the modes are nearly consistent with one another. In the case 3, it is seen that an effect of the ratio of the wall thickness to the radius, that is, the shape of the spherical shell is markedly manifested.

In the present example, based on the foregoing results of the calculation, the signal processing unit adopts a technique of determining the dimensionless vibration frequency $\beta_n$ of the ellipsoidal shell using the major-axis radius-vs.-minor-axis radius ratio of the ellipsoid. The detailed flow of step 15 in FIG. 2 in the case of the second example will be described below in conjunction with FIG. 11. The configuration of the device of the second example is identical to the configuration of the device of the first example. The processing flow of the present example is identical to the processing shown in FIG. 2. However, in the processing flow of the signal processing unit 15, the details of step 13 and step 15 are different. Therefore, the steps 13 and 15 will be described below.

Figure 10:
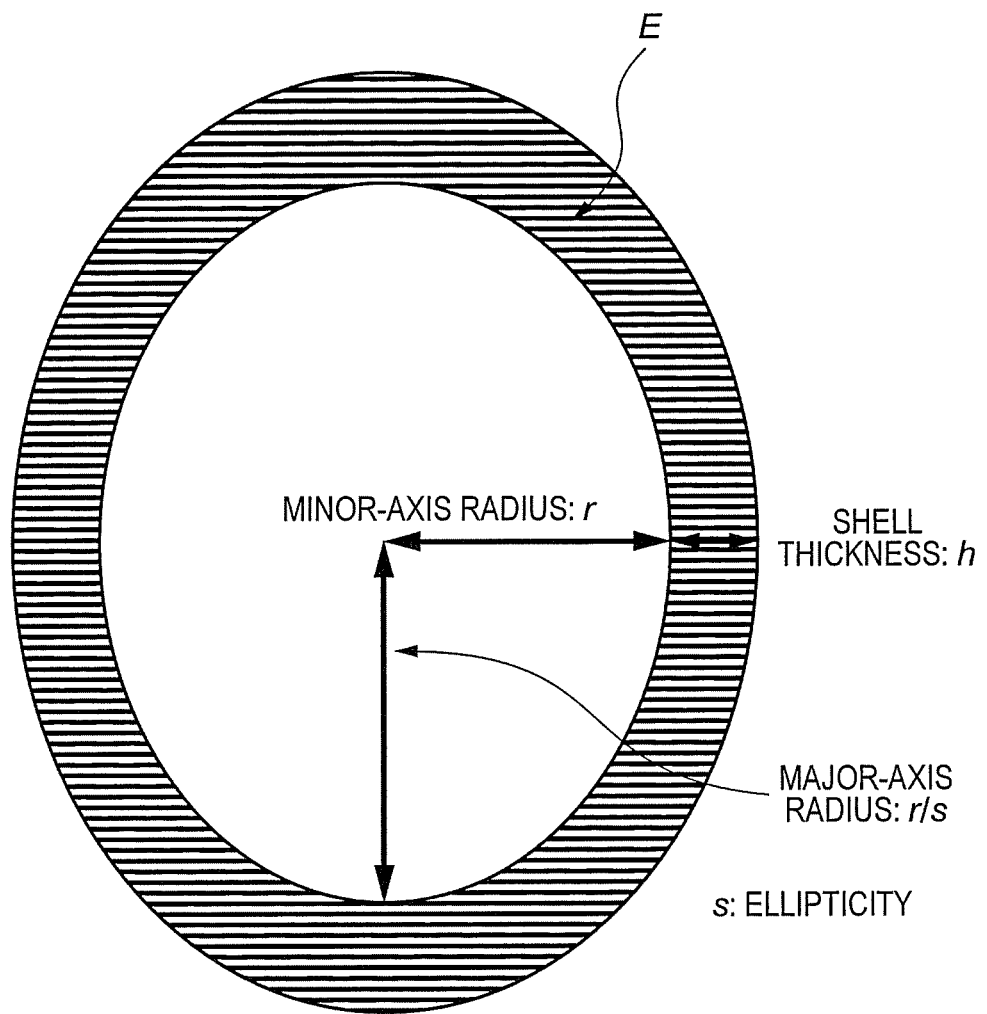
FIG. 10 is a schematic diagram for explaining an ellipsoidal shell which relates to the second example.

First, at step 13 in the present example, positional information on a tissue image obtained at step 11 is detected through image processing. More particularly, since a tissue in an ultrasonic image is recognized as a high luminance value, a high-luminance value portion is regarded as a cardiac tissue, and a two-dimensional or three-dimensional cardiac-tissue position is acquired. Further, if an examining person finds it necessary, the shape extraction block 152 approximates shape parameters, which define the shape of the heart or each heart chamber that is part of the heart, that is, as shown in FIG. 10, an inner radius r [m] and cardiac wall thickness [m] with the heart chamber wall as an ellipsoid, and calculates a major-axis radius-vs.-minor-axis radius ratio s (herein s is equal to or smaller than 1). The inner radius r and cardiac wall thickness h may be averages among the heart chambers or local values. An ellipsoid approximation method for a heart chamber may be pattern matching of the volume of the heart chamber, a heart chamber section of an ellipsoidal body, and an ellipsoid.

Thereafter, at step 15 in the present example, the arithmetic block 154 of the signal processing unit 15 approximates a heart chamber to an ellipsoidal shell, and employs the laws of physics concerning the ellipsoidal shell and an eigen-vibration frequency.

Figure 11:
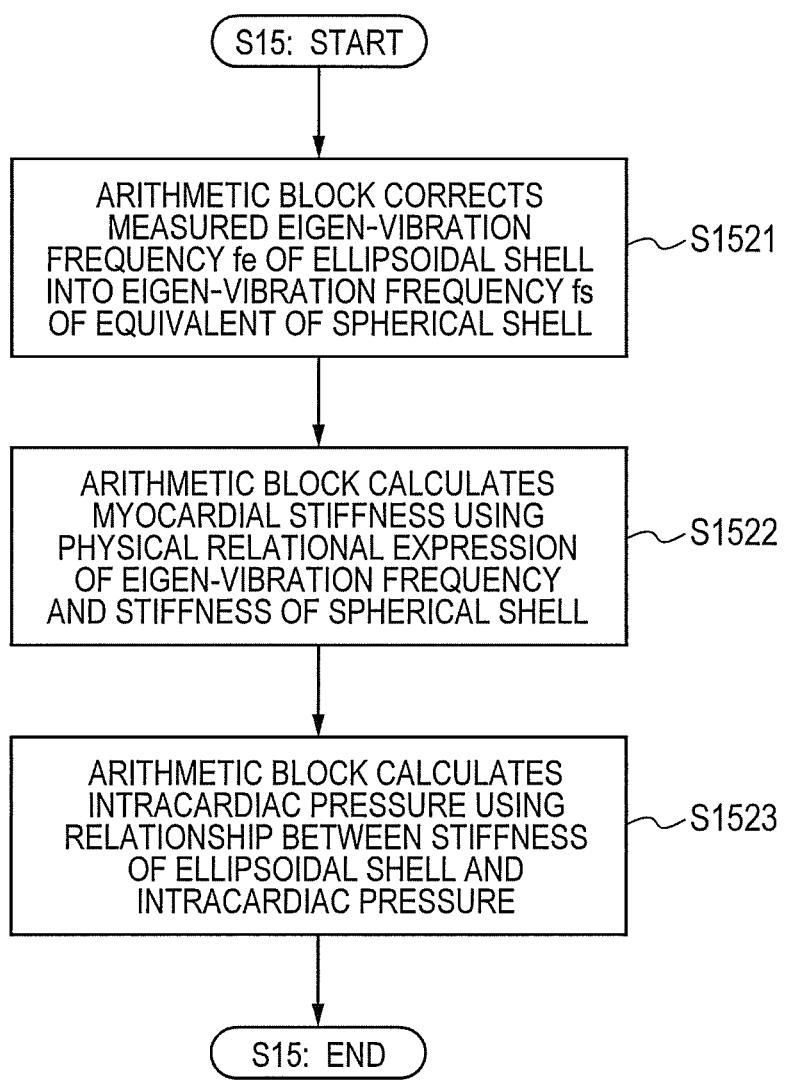
FIG. 11 is a flowchart presenting an example of actions of a signal processing unit and relating to the second example.

FIG. 11 shows a detailed flow of step 15. At step 1521, the arithmetic block 154 corrects a measured eigen-vibration frequency $f_{e,n}$ [Hz] of an ellipsoidal shell in a mode n into an eigen-vibration frequency $f_{s,n}$ [Hz] of an equivalent of a spherical shell in the mode n. Herein, for calculation of the eigen-vibration frequency $f_{s,n}$ of the equivalent of the spherical shell in the mode n, the vibration frequency ratio F between the spherical shell and ellipsoidal shell shown in each of FIG. 9A, FIG. 9B and FIG. 9C may be used for correction, or an eigen-vibration dimensionless value $\beta_{e,n}$ of the ellipsoidal shell may be used directly.

For calculation of the value $\beta_n$, a numerical solution may be obtained using the finite element method or an analytical solution may be obtained using a Mathieu function. The vibration frequency ratio F or dimensionless value $\beta_n$ are, as described later, stored in advance in the memory 155 of the signal processing unit 15 in FIG. 1 as a table, fitting function, or analytic function.

$$f_{s,n} = \frac{f_{e,n}}{F} \quad \text{(formula 6)}$$

Thereafter, the arithmetic block 154 calculates the stiffness of the cardiac muscle using a physical relational expression of an eigen-vibration frequency and the stiffness of a spherical shell expressed as the formula (3) (S1522). The formula (3) may be simplified and a resultant formula (7) may be employed. The stiffness E is calculated from the eigen-vibration frequency $f_{s,n}$ of the spherical shell in the mode n.

$$E = C_c r^2 f_{s,n}^2 \quad \text{(formula 7)}$$

$$C_c = \frac{(2\pi)^2 \rho (1-v^2)}{\beta_n^2}$$

where a coefficient $C_c$ takes on a constant determined individually for the heart according to the formula (7). A value the coefficient takes on for the typical heart ranges from $6\times10^4$ to $4\times10^5$ [kg/m$^3$]. FIG. 9D shows an example of tables of the resultant vibration frequency ratios F. The upper part of FIG. 9D shows the table for the mode 2X, and the lower part thereof shows the table for the mode 2R.

Similarly to the vibration frequency ratio F, a dimensionless parameter $\beta_{e,n}$ may be calculated in advance from parameters r, $f_{e,n}$, E, and $\rho$, which are used for calculation in the finite element method, according to the finite element method, and stored in the memory 155 as a table, fitting function, or analytic function. At the time of actual measurement, the stiffness E may be obtained according to a formula (9). FIG. 9E shows an example of a table of the dimensionless parameters $\beta_{e,n}$. The table for the mode 2x is presented as an example.

$$B_{e,n} = rf_{e,n}\sqrt{\frac{\rho}{E}} \quad \text{(formula 8)}$$

$$E = \rho\left(\frac{rf_{e,n}}{B_{e,n}}\right)^2 \quad \text{(formula 9)}$$

Based on the stiffness E of the cardiac muscle calculated according to the formula (9), an intracardiac pressure is calculated using a relational expression (10) below of a myocardial stiffness of an ellipsoidal shell and an intracardiac pressure thereof.

$$E = \left(\delta\alpha V + \frac{1+G}{1 - \frac{h}{r(2-s^2)}}\right)\sigma \quad \text{(formula 10)}$$

$$\sigma = p\frac{h}{r}\left(\left(1 - \frac{s^2}{2}\right) - \frac{h}{2r}\right)$$

$$\left.\begin{array}{l} G = \dfrac{a_1 V_w - b_1 V}{a_2 V_w + b_2 V} \\[4pt] \delta = \left(2 + \dfrac{Gh}{r}\right)\left(1 + \dfrac{h}{2r} + \dfrac{h^2}{4r^2}\right) + \left(1 + \dfrac{Ghs}{2r}\right)\left(1 + \dfrac{hs}{2r}\right) \\[4pt] a_1 = 3 - \dfrac{h}{r} - \dfrac{hs}{2r} + \dfrac{h^2}{2r^2} \\[4pt] b_1 = \dfrac{hs}{r} + \dfrac{2h}{r} \\[4pt] a_2 = \dfrac{h}{r}\left(1 - \dfrac{h}{2r} + \dfrac{h^2}{4r^2}\right) + \dfrac{hs}{2r}\left(1 - \dfrac{hs}{2r}\right) \\[4pt] b_2 = \dfrac{h}{r}\left(2 + \dfrac{h^2}{2r^2}\right) + \dfrac{hs}{r} \end{array}\right\} \quad \text{(formula 11)}$$

where V denotes the volume of the lumen of a heart chamber, and $V_w$ denotes the volume of the wall of the heart chamber. In addition, $\alpha$ denotes a coefficient experimentally obtained and expressed as a formula (12). $C_p$ denotes a coefficient of 57.3 Pa.

$$\alpha V = \ln(p/c_p) \quad \text{(formula 12)}$$

Referring back to FIG. 11, an intracardiac pressure is finally calculated from the obtained stiffness using a relational expression of the myocardial stiffness of the ellipsoidal body and the intracardiac pressure thereof (S1523). When the intracardiac pressure is not calculated, step 1523 may be omitted.

When a heart chamber can be recognized as a spherical shell, the stiffness of the heart may be calculated using formulae (13) and (14).

$$E = 3\left(1 + \frac{V_m}{V}\frac{r^2}{r^2+h^2}\right)(1+\alpha V)\sigma \quad \text{(formula 13)}$$

$$\sigma = p\frac{V}{V_w}\left(1 + \frac{h^3}{2r^3}\right) \quad \text{(formula 14)}$$

Further, a formula (15) is obtained using the formulae (12), (13), and (14).

$$E = 3\frac{V}{V_w}\left(1 + \frac{V_w}{V}\frac{r^2}{r^2+h^2}\right)\left(1 + \frac{h^3}{2r^3}\right)(1+\ln(p/c_p))p \quad \text{(formula 15)}$$

The formula (15) is an implicit description concerning an intracardiac pressure p, that is, a description requiring generally numerical repetitive calculation to obtain a solution. Herein, when a fitting relational expression (16) is employed, the intracardiac pressure p of the formula (17) can be implicitly obtained, that is, the intracardiac pressure p on the left side can be outputted merely by inputting parameters onto the right side. Accordingly, a numerical calculation time can be shortened.

$$\left(1 + \ln\left(\frac{p}{c_p}\right)\right)\frac{p}{c_p} \cong \frac{9}{4}\left(\frac{p}{c_p}\right)^{6/5} \quad \text{(formula 16)}$$

$$p = c_p\left(\frac{\dfrac{4E}{27c_p}\dfrac{V_w}{V}}{\left(1 + \dfrac{V_w}{V}\dfrac{r^2}{r^2+h^2}\right)\left(1 + \dfrac{h^3}{2r^3}\right)}\right)^{5/6} \quad \text{(formula 17)}$$

Further, using the formulae (7) and (17), the intracardiac pressure p may be calculated by inputting shape parameters.

EXAMPLE 3

Next, an ultrasonic imaging device of the third example will be described below. In the first example, the finite element method is repetitively used to calculate a myocardial stiffness and intracardiac pressure. In the third example, iteration is not used to calculate the myocardial stiffness and intracardiac pressure. Specifically, the present example is the ultrasonic imaging device that images an object by utilizing ultrasonic waves, and includes an ultrasonic probe that transmits or receives ultrasonic waves to or from the heart which is an object, a signal processing unit that processes a reflected echo signal received by the ultrasonic probe, and a display unit that displays the results of signal processing performed by the signal processing unit. The signal processing unit includes a shape extraction block that extracts shape information on the heart from the reflected echo signal, and an eigen-vibration detection block that detects an eigen-vibration frequency of the heart by performing finite element calculation using the shape information. Using the obtained eigen-vibration frequency and measured eigen-vibration frequency, the stiffness of the cardiac muscle or an intracardiac pressure thereof is calculated using a relational rule between the eigen-vibration frequency and the stiffness of the cardiac muscle. The configuration of the ultrasonic imaging device of the present example is identical to that of the device in FIG. 1 described in relation to Example 1. A difference lies in processing of the signal processing unit 15 of the device in FIG. 1. As described later, the difference from the device in FIG. 1 is step 15 of the processing flow described in FIG. 2.

A dominant equation representing an eigen-vibration frequency of a spherical shell is expressed as the formula (2) (Non-patent Literature 2). $\beta_n$ denotes a variable that is a dimensionless value of an eigen-vibration frequency $f_n$. $C_{6a}$, $C_{4a}$, $C_{2a}$, $C_{0a}$, $C_{6b}$, $C_{4b}$, $C_{0b}$, $C_a$ and $C_b$ denote nine constants determined with a ratio of a wall thickness to an inner diameter, h/r, which implies a shape, and a Poisson ratio $C_b$. $J_n(x)$ and $J_n'(x)$ denote a spherical Bessel function of the n-th kind of a variable x and its derivation. According to the formula (5) presented in Example 2, the $\beta_n$ value does not depend on the value of a tissular stiffness E but remains unchanged all the time. Once a shape and the Poisson ratio are determined, the $\beta_n$ value is determined. This conclusion deduced from the spherical shell implies a possibility that even when the general shape of the heart is concerned, once the shape is determined, the $\beta_n$ value is determined irrespective of the E value. In the present example, the possibility that once a shape is determined, the $\beta_n$ value is determined irrespective of the E value is extended to the general shape of the heart.

An extension method in the present example will be described below. $\beta$ in the formula (3) denotes a value that is uniquely determined as long as a shape is determined. Namely, if the shape is a similarity shape, $\beta$ takes on the same value. This is expressed as a formula (18). Herein, subscripts A, B, C, and D denote cases that are different from one another in a size and stiffness. The $\beta$ value is identical among the cases. A subscript true denotes a true value of the stiffness of the cardiac muscle or an eigen-vibration frequency which a user wants to measure.

$$\beta = C_d \frac{f_A}{E_A^{1/2}} = C_d \frac{f_B}{E_B^{1/2}} = C_d \frac{f_C}{E_C^{1/2}} = C_d \frac{f_D}{E_D^{1/2}} = C_d \frac{f_{true}}{E_{true}^{1/2}} \quad \text{(formula 18)}$$

When the formula (18) is deformed, it is rewritten as a formula (19). Even when an arbitrary value Ea is set, a true value Etrue of the stiffness of the heart can be obtained using the eigen-vibration frequency fa obtained according to the finite element method and the eigen-vibration frequency ftrue obtained through measurement.

$$E_{true} = E_A \frac{f_{true}^2}{f_A^2} \quad (19)$$

Figure 13:
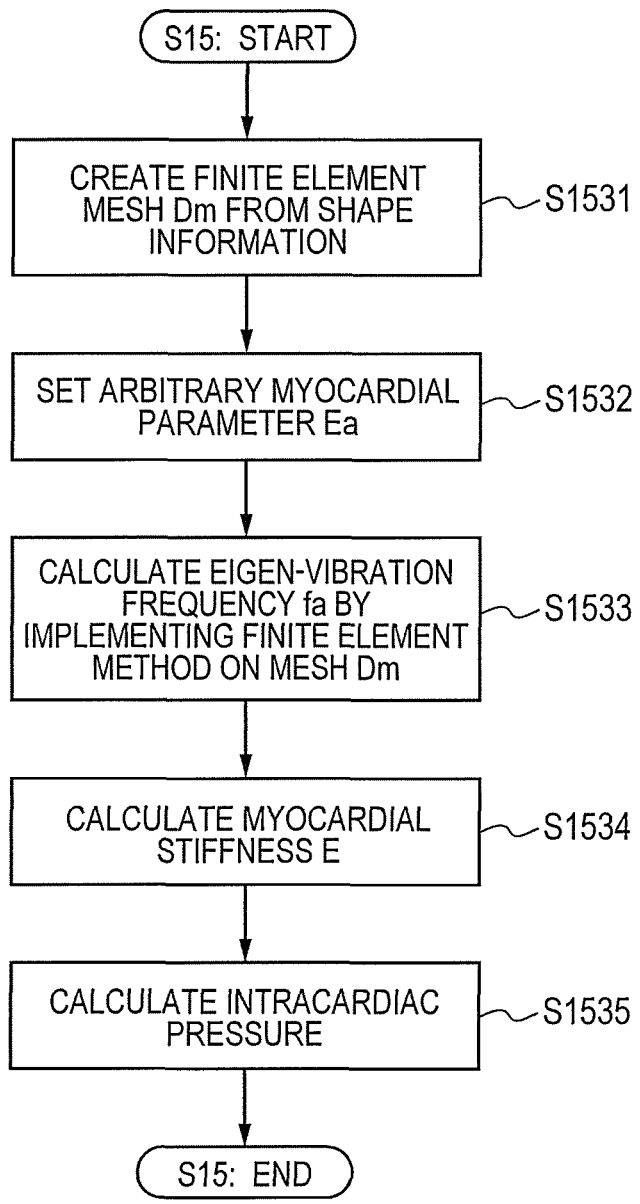
FIG. 13 is a flowchart presenting an example of actions of a signal processing unit and relating to a third example.

Referring to FIG. 13, detailed processing of the finite element method in the present example will be described below. The arithmetic block 154 creates a finite element mesh Dm from shape information Do extracted by the shape extraction block 152 (S1531). Thereafter, an arbitrary myocardial stiffness EA is set (S1532), and the produced finite element mesh Dm is used to calculate an eigen-vibration frequency fA (S1533). The arbitrary myocardial stiffness EA may be inputted at the input unit by a user or may be stored in the memory. Thereafter, using the formula (19), the myocardial stiffness E is calculated from the measured eigen-vibration frequency (S1534). Thereafter, using the formula (12), an intracardiac pressure p is calculated based on an internal volume V calculated from shape information (S1535).

Various examples of the present invention have been cited and described so far. Needless to say, the present invention is not limited to the examples. For example, even in a case where reflected echo signal data produced by accumulating a signal obtained by shaping a reflected echo signal, which is received by the ultrasonic probe included in the aforesaid ultrasonic imaging device, in the ultrasound receiving circuit is employed, and processed using an information processing device such as an ordinary computer including a signal processing unit, memory unit, display unit, and input unit, when the aforesaid present invention is utilized, information on the stiffness of the heart of a desired subject or an intracardiac pressure thereof can be highly precisely acquired.

Industrial Applicability

The present invention relates to an ultrasonic imaging device for medical use or an information processing device, and proves quite useful as an ultrasonic imaging technology for measuring the stiffness of the heart, which is desired by an examining person, or an intracardiac pressure thereof.

REFERENCE SIGNS LIST

1: Main body
2: Ultrasonic probe
3: Living body
10: Input unit
11: Control unit
12: Ultrasonic signal generator
13: Ultrasound receiving circuit
14: Display unit
15: Signal processing unit
31: Left ventricle
32: Left atrium
33: Right ventricle
34: Mitral valve
35: Posterior wall of left ventricle
36: Apex cordis
37: Ultrasonic scanning line
38, 39: Eigen-vibration frequency
61: Mitral valve inflow velocity
62: Pulmonary-artery valve regurgitation velocity
63: Pulmonary-artery valve regurgitation velocity
64: Cardiac wall motion velocity
65: Cardiac wall motion
66: End diastole
67: Ellipsoidal shell

The invention claimed is:

1. An ultrasonic imaging device that images an object by utilizing ultrasonic waves, comprising:
    an ultrasonic probe that transmits or receives ultrasonic waves to or from the heart that is the object;
    a signal processing unit that processes a reflected echo signal received by the ultrasonic probe; and
    a display unit that displays results of signal processing performed by the signal processing unit, wherein
    the signal processing unit includes
    a shape extraction block that extracts chamber-circumscribing shape information outlining walls of a chamber of the heart from the reflected echo signal;
    an eigen-vibration detection block that detects an eigen-vibration of the heart from the reflected echo signal; and an arithmetic block that calculates a myocardial stiffness of the heart or an intracardiac pressure thereof from the chamber-circumscribing shape information and eigen-vibration, wherein the eigen-vibration detection block detects one or more predetermined eigen-vibration modes of a heart chamber shape of the heart which is obtained as the chamber-circumscribing shape information by the shape extraction block, and calculates an eigen-vibration frequency that is a frequency in the eigen-vibration mode, and wherein the arithmetic block calculates the myocardial stiffness or intracardiac pressure using a plurality of eigen-vibration modes calculated by the eigen-vibration detection block;

wherein the signal processing unit is configured to perform operations to: create a finite element mesh from the chamber-circumscribing shape information, create a scaled shape mesh by applying a scaling factor to the finite element mesh, use the scaled shape mesh to calculate a calculated eigen-vibration frequency, measure an eigen-vibration frequency to determine a measured eigen-vibration frequency, and determine a difference between the calculated eigen-vibration frequency and the measured eigen-vibration frequency; and wherein the signal processing unit is further configured to repeat the operations using a changed scaling factor until the difference between the calculated eigen-vibration frequency and the measured eigen-vibration frequency is within a predetermined threshold difference.

2. The ultrasonic imaging device according to claim 1, wherein the eigen-vibration detection block determines a detection point for the eigen-vibration mode of the heart chamber shape.

3. The ultrasonic imaging device according to claim 1, wherein the arithmetic block performs finite element calculation using a relational rule among the chamber-circumscribing shape information, myocardial stiffness, and intracardiac pressure so as to calculate the intracardiac pressure or the myocardial stiffness.

4. The ultrasonic imaging device according to claim 1, wherein the shape extraction block approximates the left ventricle of the heart to an ellipsoidal shell, and calculates an inner diameter on the minor axis or major axis of the ellipsoidal shell, a shell thickness, and a major-axis radius-vs.-minor-axis radius ratio.

5. The ultrasonic imaging device according to claim 4, wherein the arithmetic block calculates the myocardial stiffness from the eigen-vibration frequency of the ellipsoidal shell.

6. The ultrasonic imaging device according to claim 5, wherein the arithmetic block performs correction so as to correct the eigen-vibration frequency of the ellipsoidal shell into that of a spherical shell.

7. The ultrasonic imaging device according to claim 5, wherein the arithmetic block uses a correction table to correct the eigen-vibration frequency of the ellipsoidal shell into that of the spherical shell.

8. The ultrasonic imaging device according to claim 5, wherein the arithmetic block calculates the intracardiac pressure using a relational rule between the myocardial stiffness and intracardiac pressure observed during approximation to the ellipsoidal shell.

9. The ultrasonic imaging device according to claim 1, wherein the signal processing unit further includes a palmic time phase detection block that detects a palmic time phase of the heart, and calculates the myocardial stiffness or intracardiac pressure in a predetermined palmic time phase detected by the palmic time phase detection block.

10. The ultrasonic imaging device according to claim 9, wherein the display unit displays a spectrum analysis diagram produced by plotting the eigen-vibration frequency of the eigen-vibration calculated by the arithmetic block, and the palmic time phase, which is detected by the palmic time phase detection block, in a two-dimensional space.

11. The ultrasonic imaging device according to claim 1, further comprising an input unit with which a predetermined point is set in an image displayed on the display unit, wherein:
the signal processing unit detects the eigen-vibration mode at the predetermined point set with the input unit.

12. The ultrasonic imaging device according to claim 1, wherein the display unit displays the myocardial stiffness or intracardiac pressure calculated by the arithmetic block.

13. The ultrasonic imaging device according to claim 1, wherein the signal processing unit performs finite element calculation using the chamber-circumscribing shape information, detects the eigen-vibration frequency of the heart, and calculates the myocardial stiffness or the intracardiac pressure using a relational rule between the eigen-vibration frequency of the heart and the myocardial stiffness.

* * * * *